United States Patent [19]
Meyerhoff et al.

[11] Patent Number: 5,981,203
[45] Date of Patent: *Nov. 9, 1999

[54] UNITARY SANDWICH ENZYME IMMUNOASSAY CASSETTE, DEVICE AND METHOD OF USE

[75] Inventors: Mark E. Meyerhoff, Ann Arbor, Mich.; Chuanming Duan, Hockessin, Del.

[73] Assignee: The Regents of the University of Michigan, Ann Arbor, Mich.

[ * ] Notice: This patent is subject to a terminal disclaimer.

[21] Appl. No.: 08/737,027

[22] PCT Filed: Apr. 26, 1995

[86] PCT No.: PCT/US95/05156

§ 371 Date: Jan. 13, 1997

§ 102(e) Date: Jan. 13, 1997

[87] PCT Pub. No.: WO95/29395

PCT Pub. Date: Nov. 2, 1995

Related U.S. Application Data

[63] Continuation-in-part of application No. 08/233,648, Apr. 26, 1994, abandoned.

[51] Int. Cl.[6] ............ G01N 33/53; G01N 27/00; G01N 33/543; A61L 5/103
[52] U.S. Cl. ............ 435/7.92; 435/5; 435/6; 435/7.1; 435/7.9; 422/82.01; 422/82.02; 427/2.11; 436/518; 436/525; 436/528; 436/807
[58] Field of Search ............ 435/5, 6, 7.1, 7.9, 435/7.92, 7.93, 7.94; 422/82.01, 82.02; 436/518, 525, 528, 807; 427/2.11

[56] References Cited

U.S. PATENT DOCUMENTS

| | | | |
|---|---|---|---|
| 4,920,047 | 4/1990 | Giaver et al. | 435/7.9 |
| 5,023,053 | 6/1991 | Finlan | 422/82.05 |
| 5,063,081 | 11/1991 | Cozzette . | |

FOREIGN PATENT DOCUMENTS

93/25909 12/1993 WIPO .

OTHER PUBLICATIONS

Armenta et al., "Improved Sensitivity in Homogeneous Enzyme Immunossays Using a Fluorogenic Macromolecular Substrate: An Assay for Serum Ferritin", *Anal. Biochem.* 146, 211–219 (1985).

Brown, Daniel V & Meyerhoff, Mark E., "Potentiometric enzyme channeling immunosensor for proteins," *Biosensors & Bioelectronics*, 6:615–622 (1991).

Chen et al., "Ultrasound–Accelerated Immunoassay, as Exemplified by Enzyme Immunossay of Choriogonado-tropin", *Clin. Chem.* 30, 1446–51 (1984).

Christie, I.M. et al., Simplified measurement of serum alkaline phosphatase utilizing electrochemical detection of 4–aminophenol, *Analytica Chimica Acta*, 257:21–28 (1992).

Gibbons et al., "Homogeneous Enzyme Immunossay for Proteins Employing J–Galactosidase", *Anal. Biochem.* 102:167–170 (1980).

Ngo et al., Separation–Free Amperometric Enzyme Immunossay, 64–70, The Humana Press, 1985.

Schray et al., "Seperation–Free Dual Solid Phase Enzyme Immunossay for Macromolecules", *Anal. Chem.*, 60 353–56 (1988).

Valkirs et al., "Immunoconcentration—a New Format for Solid–Phase Immunossays", *Clin. Chem.* 31:1427–31 (1985).

Valkirs et al., "Qualitative Two–site IEMA for Serum hCG Using Immunoconcentration Technology", *Clin. Chem.* 31:960 (1985).

Cheng et al., "Selectivity and Sensitivity of Self–Assembled Thiotic Acid Electrodes," *Anal. Chem.* 64(9):1998–2000, 1992.

Duan et al., "Separation–Free Sandwich Enzyme Immunossays Using Microporous Gold Electrodes and Self–. . . ," *Anal. Chem.* 66(9):1369–1377, May 1, 1994.

Nakans et al., "New Bifunctional Dialkyl Disulfide Reagent for the Fabrication of a Gold Surface . . .," *Anal. Sci.* 9:133–136, 1993.

*Primary Examiner*—James C. Housel
*Assistant Examiner*—Rodney P. Swartz
*Attorney, Agent, or Firm*—Morrison & Foerster LLP

[57] ABSTRACT

An enzyme sandwich immunoassay, device and cassette therefor for determining a target analyte are described. The enzyme sandwich immunoassay cassette (B) comprises a microporous membrane support (m) having coated thereon a conductive metal layer overlaid with a capture antibody layer (e). The electrochemical device (A) comprises a first chamber (b) into which sample and an enzyme labelled antibody capable of specifically binding to the target analyte are placed, wherein the enzyme is capable of catalyzing the production of an electrochemically detectable product; a second chamber (a) adjoining the first chamber (b) into which a substrate for the enzyme is placed, wherein the substrate is capable of producing, when catalyzed by the enzyme, the electrochemically detectable product; and, separating the first (b) and second (a) chambers, a microporous membrane support (m) as described above, wherein the conductive metal layer (e) of the microporous membrane support (m) acts as an electrode to detect, directly or indirectly, the presence of the electrochemically detectable product.

14 Claims, 15 Drawing Sheets

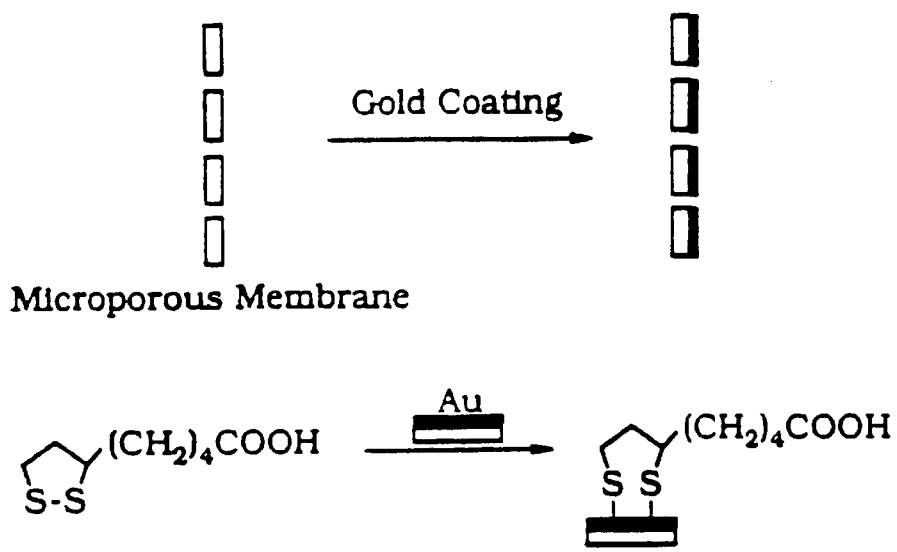
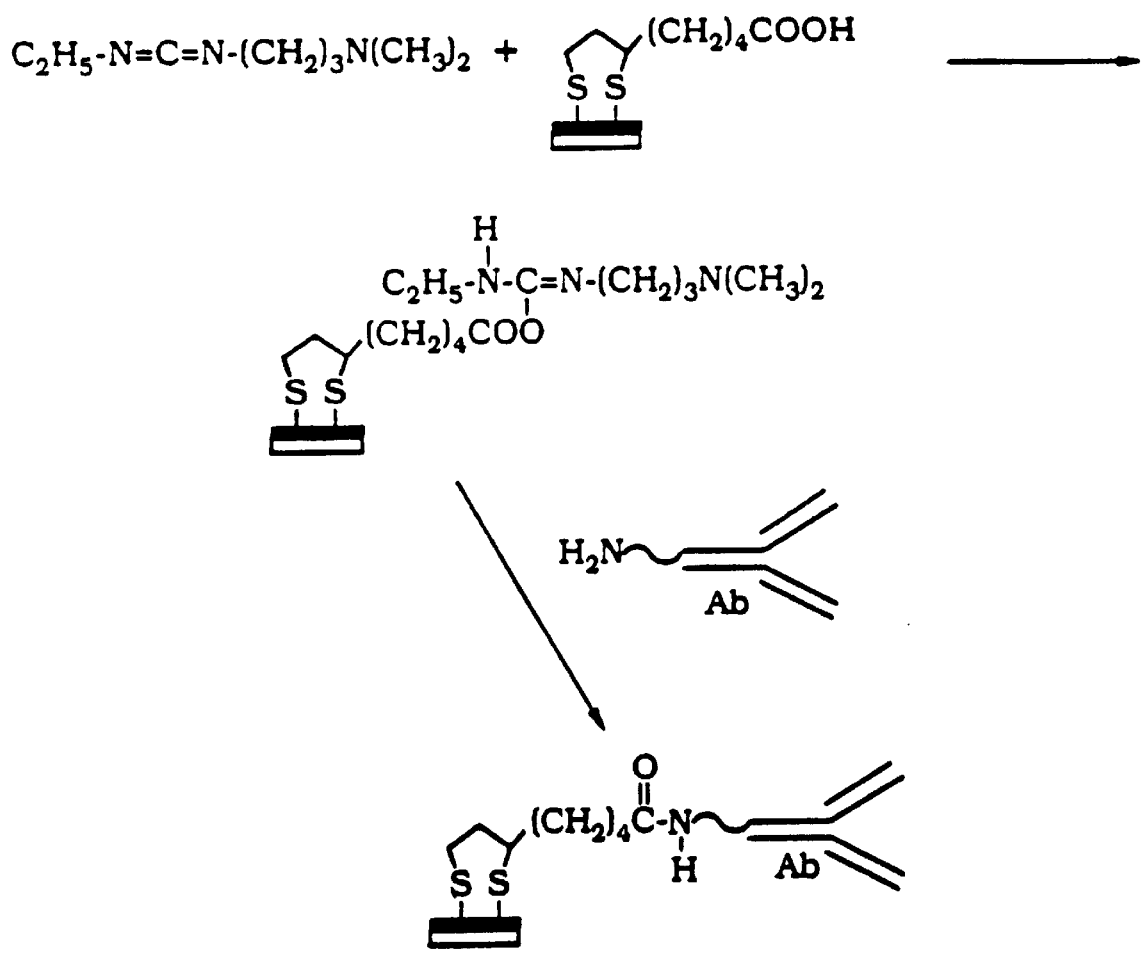
FIG. 3

UNITARY SANDWICH ENZYME IMMUNOASSAY CASSETTE, DEVICE AND METHOD OF USE

The present application represents the United States national stage, 35 USC section 371, of PCT/US95/05156, internationally filed on Apr. 26, 1995 while designating the United States, and which represents a continuation-in-part of U.S. application Ser. No. 08/233,648, filed Apr. 26, 1994, now abandoned but whose priority is claimed.

This invention was made in part with government support under grant CHE9119728 awared from the National Science Foundation. The United States government has certain rights in this invention.

FIELD OF THE INVENTION

The present invention relates to certain sandwich-type immunoassay devices and their use. In particular, the invention relates to an enzyme immunoassay using an electrochemical means of detection that allows for a non-separation assay format.

BACKGROUND ART

Enzyme immunoassays (EIA) have become important analytical methods in clinical chemistry laboratories for the selective detection of drugs, hormones, and proteins at trace levels. As specific examples, such methods are now used routinely to detect diagnostically important blood proteins, including creatine kinase-MB to detect the occurrence of myocardial infarctions, prostate-specific antigen (PSA) to screen for prostate cancer, and human chorionic gonadotropin (hCG) to confirm pregnancy. Further, such methods can be used to detect the protein coat of a specific virus. Thus, the invention also has utility for assays in agriculture and the food processing industry, for example, in-line monitoring of a food processing plant.

One of the must useful of the immunoassays is the two-antibody sandwich technique, which is used primarily to determine the presence and concentration of an antigenic analyte in an unknown sample. Two-antibody assays can be relatively quick, particularly if a source of pure antigen is available. The assay requires two antibodies that bind to non-overlapping epitopes on the antigenic analyte. Either two monoclonal antibodies that recognize discrete sites or one batch of affinity-purified polyclonal antibodies can be used.

To use the conventional two-antibody assay, a "capture" antibody is purified and bound to a solid phase, and the antigenic analyte in a standard or test sample solution is allowed to bind to the capture antibody. Unbound analyte proteins are then typically removed by washing. A second antibody, which is labeled with an enzyme, is allowed to bind to the immuno-bound analyte. After another wash step to remove the excess enzyme-labeled antibody, the amount of enzyme label bound to the matrix is determined, usually by adding a substrate on which the enzyme acts and measuring the rate of product generated. The rate that product is generated is directly proportional to the amount of the antigenic analyte present in the sample.

This sandwich-type assay is superior to other types of solid phase immunoassays with respect to sensitivity, specificity and kinetics. These advantages arise from the fact that excess amounts of the capture antibody and the enzyme-antibody conjugate are used relative to the low levels of the analyte commonly present, thus driving the equilibrium of the binding reaction toward the formation of the sandwich structure.

An EIA method can be heterogeneous or homogeneous, depending on whether or not washing steps are required to separate free and bound enzyme label. EIA's can also be competitive or non-competitive, depending on the availability of antibody binding sites. Of these different EIA methods, non-competitive heterogeneous sandwich assays have the advantage of using two co-existing determinant sites on the same antigenic analyte to be detected. As a result, these sandwich-type assays generally exhibit good specificity when identifying the presence and/or amount of protein analytes. Further, due to the innate amplification properties of enzymes, the use of EIA offers excellent sensitivity.

Even though sandwich-type EIA's are used widely in clinical laboratories, such methods usually require multiple wash steps to separate the excess amounts of reagents used from the sandwich being formed. This has created a need for complex instrumentation to do a high volume of immunoassay tests. Thus, the need to limit the wash steps has made it very difficult to adapt these assays into portable test systems that would be desirable for detecting diagnostically important proteins in field locations, such as doctors' offices, emergency vehicles, and hospital "crash" carts.

Another problem has been the length of time required for incubation to accomplish sufficient binding between wash steps. While immunoconcentration techniques using capture antibodies immobilized on glass and other filter material have reduced the binding incubation times usually associated with sandwich-type EIA's, discrete separation and wash steps are still required. For example, the use of suspensions of particles possessing immobilized antibodies can greatly enhance the speed of immmobinding. However, then, additional filtering or centrifugation steps are required.

Further, such immunoconcentration methods are only useful for detecting proteins found in the circulatory system when the red blood cells have been removed. Serum and plasma samples are required, rather than whole blood, because the presence of red blood cells clogs the filter-based devices used in immunoconcentration techniques. See Valkirs et al., "Qualitative Two-site IEMA for Serum hCG Using Immunoconcentration Technology", *Clin. Chem.* 31, 960 (1985) and Valkirs et al., "Immunoconcentration—a New Format for Solid-Phase Immunoassays", *Clin. Chem.* 31, 1427–31 (1985).

The development of a rapid, simple, non-separation method for the detection of proteins has been a long-standing goal. Gibbons et al., "Homogeneous Enzyme Immunoassay for Proteins Employing β-Galactosidase", *Anal. Biochem.* 102, 167–170 (1980), and Armenta et al., "Improved Sensitivity in Homogeneous Enzyme Immunoassays Using a Fluorogenic Macromolecular Substrate: An Assay for Serum Ferritin", *Anal. Biochem.* 146, 211–219 (1985), used chromogenic and fluorogenic galactoside-dextran substrates in devising homogeneous enzyme immunoassays for C-reactive protein, ferritin, and immunoglobulins. However, the low degree of modulating enzyme activity in this homogeneous protocol has rendered the method impractical for real world applications.

Chen et al., "Ultrasound-Accelerated Immunoassay, as Exemplified by Enzyme Immunoassay of Choriogonadotropin", *Clin. Chem.* 30, 1446–51 (1984), combined a two-enzyme channeling technique with immunocapillary migration to produce a test-strip format for the detection of hCG. Although wash steps were not required, this approach is not truly separation-free, since the test trip has to be removed from the sample before adding the enzyme substrate.

Schray et al., "Separation-Free Dual Solid Phase Enzyme Immunoassay for Macromolecules", *Anal. Chem.*, 60 353–56 (1988), have reported a separation-free dual solid-phase enzyme immunoassay for macromolecules, which relies on the partitioning of an enzyme conjugate (biotin-glucose-6-phosphate dehydrogenase-antibody) between two solid phases of polystyrene latex-bound avidin and polystyrene latex-bound analyte. However, this assay scheme requires 24 hours for enzymatic generation of a detectable product.

It has long been recognized that coupling electrochemical detection with EIA's would be advantageous. Electrodes are insensitive to the color or turbidity of a test sample, and thus can be used to develop methods directly applicable to whole blood samples. However, most of the many reports regarding the use of electrochemical detection to devise EIA's or "immunosensors" have relied on using such sensors as solid phases in heterogeneous assay arrangements in which antibodies are immobilized at the surface of a given electrode. After incubation of a sample with other reagents, the surface of the electrodes have to be washed before adding the substrate needed to measure bound enzyme activity.

As a specific example, Cozzette et al., U.S. Pat. No. 5,063,081 issued Nov. 5, 1991, discloses a ligand/ligand receptor-based biosensor for detecting a particular analyte species, such as an antigen. A base sensor comprises a catalytic indicator electrode, using a noble late transition metal, such as iridium, gold, platinum, silver and the like, is surrounded by a combined reference and counter electrode made of, for example, silver and silver chloride. (Columns 25–26.) An antibody is immobilized on the base sensor. The resulting biosensor is then brought into contact with a mixture comprising the sample and a second analyte-specific antibody, which is labeled. (Columns 45–46.) A permselective silane layer may also be used as a screen against interfering species. However, unbound materials and interfering electroactive species are preferably removed from the sensor by using either a wash solution or by using the solution containing the enzyme substrate as a wash. (Columns 47–49.)

Others using electrochemical detection methods have performed conventional heterogeneous sandwich assays by physically separating the immobilized capture antibodies, for example, in microwells or immunocolumns, from the step of electrochemically detecting the bound enzyme-antibody conjugate activity. Because the enzyme-antibody conjugate is typically present in excess, detection systems are not usually able to discriminate between the relatively small amounts of immuno-bound enzyme label and the relatively high background levels of the enzyme-labeled antibody conjugate.

Therefore, despite all of the past and current research activity in this area, there is still no single electrochemical EIA approach that enables the detection of proteins in a sample as complex as whole blood without the need to perform multiple wash steps and/or other manipulative procedures to separate the analyte and antibody materials from the substrate used to indicate the activity of a labelling enzyme. Such a non-separation EIA for proteins has long been desired.

It has now been discovered that, if the enzyme substrate is delivered only to the enzyme that is bound to the solid phase in the form of the sandwich, without simultaneously supplying substrate to the excess free enzyme-antibody conjugate in the bulk solution in any significant amount, there is no need to separate the unbound label from the bound species. Further, if the product of the enzyme reaction can be detected at the surface of a solid phase detector immediately after it is formed by spatial resolution, the analytical signal originating at the surface of the solid phase can be greatly enhanced as compared to the background signal originating from the bulk solution.

DISCLOSURE OF THE INVENTION

According to the present invention, there has been produced a novel enzyme sandwich immunoassay cassette comprising a microporous membrane support having coated thereon:

(a) a conductive metal layer; and (b) a capture antibody layer over the conductive metal layer.

Further, a device for performing an enzyme sandwich immunoassay for a predetermined analyte has been produced. The device comprises:

(a) a first chamber into which an antibody for the analyte is placed, wherein the antibody is conjugated with an enzyme and wherein the enzyme is capable of catalyzing the production of an electrochemically detectable species;

(b) a second chamber adjoining the first chamber and into which a substrate for the enzyme is placed, wherein the substrate is capable of producing, when catalyzed by the enzyme, an electrochemically detectable species; and (c) separating the first and second chambers, a microporous membrane support as described above, wherein the conductive metal layer of the microporous membrane acts as an electrode to detect, directly or indirectly, the presence of the electrochemically detectable species.

Further still, a method has been found for performing an enzyme sandwich immunoassay for a predetermined analyte comprising:

(a) contacting one side of the microporous membrane support described above with a sample known to contain, or suspected of containing, the analyte;

(b) incubating the capture antibody layer of the microporous membrane support described above with analyte in the presence of a second antibody, wherein the second antibody is conjugated with an enzyme that is capable of catalyzing the production of an electrochemically detectable species;

(c) placing on the other side of the microporous membrane a substrate for the enzyme, wherein the substrate is capable of producing, when catalyzed by the enzyme, an electrochemically detectable species; and (d) using the conductive metal layer as a working electrode to detect the presence of the electrochemically detectable species.

By this method, antibody-bound enzyme is spatially distinguishable from the bulk solution for selective detection.

BRIEF DESCRIPTION OF DRAWINGS

The present invention will be more clearly understood by referring to the following drawings, in which:

FIG. 3 shows a sequence of steps used to immobilize antibody on a microporous metal electrode.

MODES OF CARRYING OUT THE INVENTION

The microporous membrane support of the invention serves as a solid phase for the sandwich EIA. The membrane also preferably serves as the support for a working electrode in a three-electrode amperometric detection system. Materials that can be used to form the microporous membrane support should be compatible with organic solvents frequently used in immobilizing the capture antibody on the conductive metal layer and should exhibit a sufficiently high tensile strength to resist tears and/or other distortions in the porous structure during manipulation.

Examples of useful microporous membranes include microporous nylon, microporous polyvinylidene difluoride, microporous polysulfone, microporous polyester, microporous polycarbonate, and regenerated cellulose membrane. However, microporous nylon is preferred because it is naturally hydrophilic, and it is commercially available in a form that is substantially free of wetting agents.

Because it is coated with a thin layer of a conductive metal, the microporous membrane support also serves as an amperometric electrochemical detector to measure surface-bound enzyme-labeled antibody. Even after the membrane has been coated with the conductive metal layer of the invention, it is still microporous, having pore sizes within the general range of from about 0.01 to about 10 microns. Even larger pore sizes are theoretically possible, being limited only by the expense of additional conductive metal being used to partially occlude the pore. A preferred average pore size is about 0.2 µm.

The conductive metal layer can comprise any one of a number of the noble and/or late transition metals. Examples of useful metals include such metals as gold, platinum, silver, rhodium, iridium, ruthenium, palladium, osmium, and copper. Gold is a particularly preferred metal.

The conductive metal layer is usually formed by sputtering tiny drops of metal, typically varying in size from about 10 to 10,000 Å. Generally, the metal drop size used will increase as the pore size of the membrane increases. Thus, the metal is formed in a layer that usually varies in thickness from about 10 Å to about 10,000 Å. Most preferably, however, the conductive metal layer is about 600 Å thick.

Figure 4:
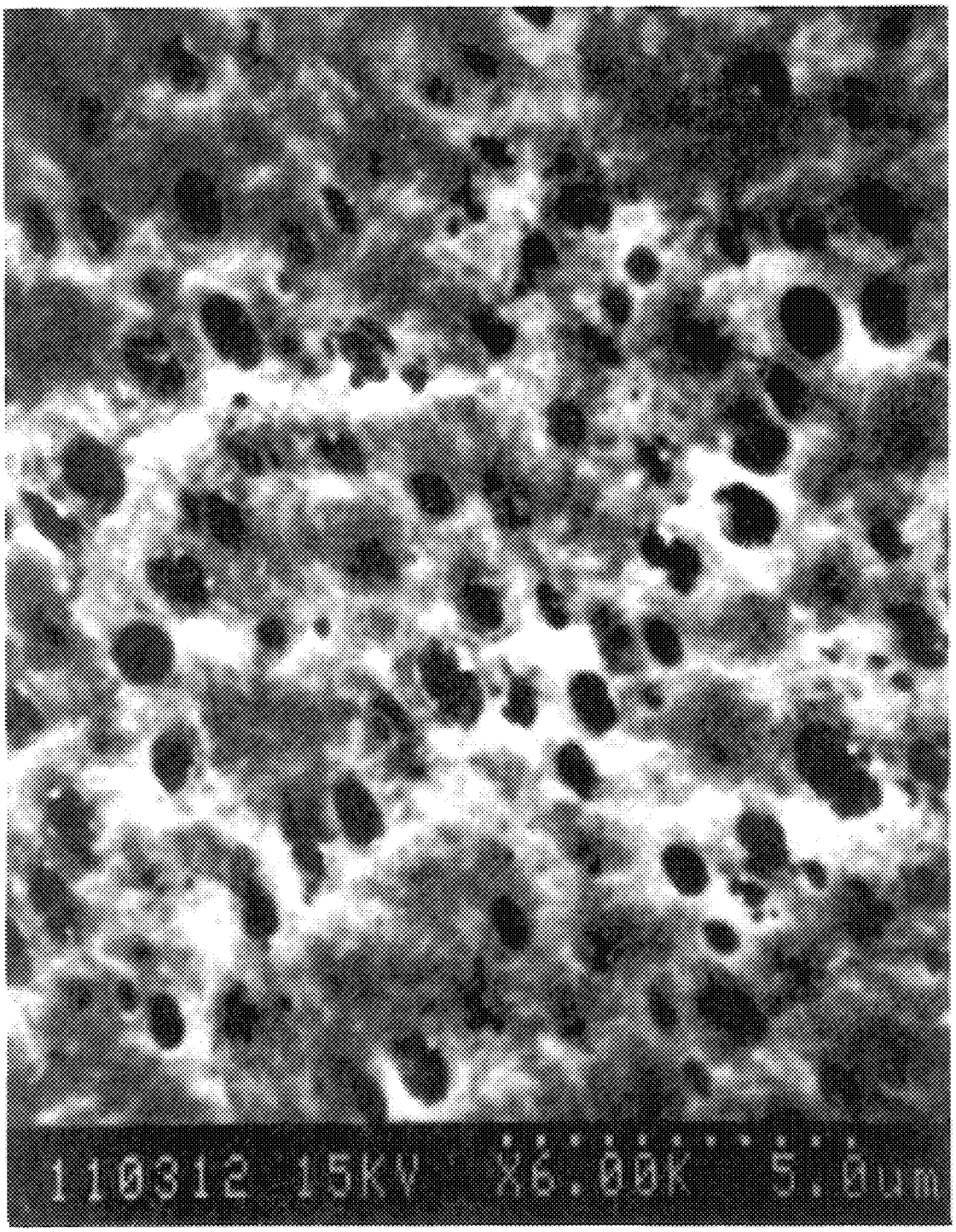
FIG. 4 shows a representation of a scanning electron micrograph of the metal-coated side of a microporous membrane.

FIG. 4 shows a scanning electron micrograph ("SEM") of a typical microporous nylon membrane in a preferred embodiment, i.e., after being coated with gold. The SEM shows that the coated areas of the metal are continuously connected with each other to make the entire 6 mm diameter disc an integrated electrode.

Antibodies that act as capture antibodies toward the antigenic or protein analyte to be measured are preferably immobilized on the metal-coated membrane, for example, via an immobilization layer such as 3-sulfhydryl propionic acid, 5-sulfhydryl pentanoic acid, 5-sulfhydryl pentamine, and thioctic acid. Preferably, there is included an immobilization layer comprising at least one compound having an -S-H group at one end and, at the other end, a group containing a carbon-oxygen bond, such as a carboxyl group or an alcohol. Most preferably, a monolayer of thioctic acid pre-adsorbed on the metal surface is used as an immobilization layer, which bonds covalently with the capture antibody.

FIG. 3 illustrates the sequence of chemical steps used to immobilize an anti-hCG antibody on a microporous metal electrode and, thus, provides a summary of antibody immobilization chemistry. The use of self-assembled layers of thioalkyl derivatives to modify metal electrodes, including for the purpose of immobilizing bioreagents, are described in further detail by Chen, *Anal. Chem.* 64, 1998–2000 (1992), and Nakano et al., *Anal. Sciences* 9, 133–36 (1993), the disclosures of which are incorporated herein by reference.

During the preparation of a microporous membrane having thereon a conductive metal layer, a layer of an insulating material such as PVC, polyurethane, silicone rubber, various epoxies, or polyethylene, is advantageously cast completely around the disc-shaped electrode to improve the reproducibility, as well as the detection limits for antibody assays. The use of such an insulator covering helps to overcome any mounting precision problems by preventing portions of the conductive metal layer from being exposed to reagent solutions. In addition, an insulating film limits the diffusion of substrate through only the area of the microporous membrane that serves as the detector. This helps to prevent contribution to the background signal from unbound antibody-conjugate in the bulk solution. The insulating layer also reduces the non-specific absorption of reagents such as proteins onto the surrounding microporous membrane, since an insulator such as PVC has a much lower nonspecific protein adsorption that a membrane such as nylon.

Another way to minimize the effect of any biological interferents present in the diffusion layer adjacent to the electrode surface, is to use a large area working electrode. Even if such interferents can be oxidized by the working electrode at the modest anodic potentials customarily used, their concentration at the electrode surface can be rapidly depleted during the three-minute period prior to adding substrate from the back side to initiate the measurement of bound enzyme-antibody.

Figure 1:
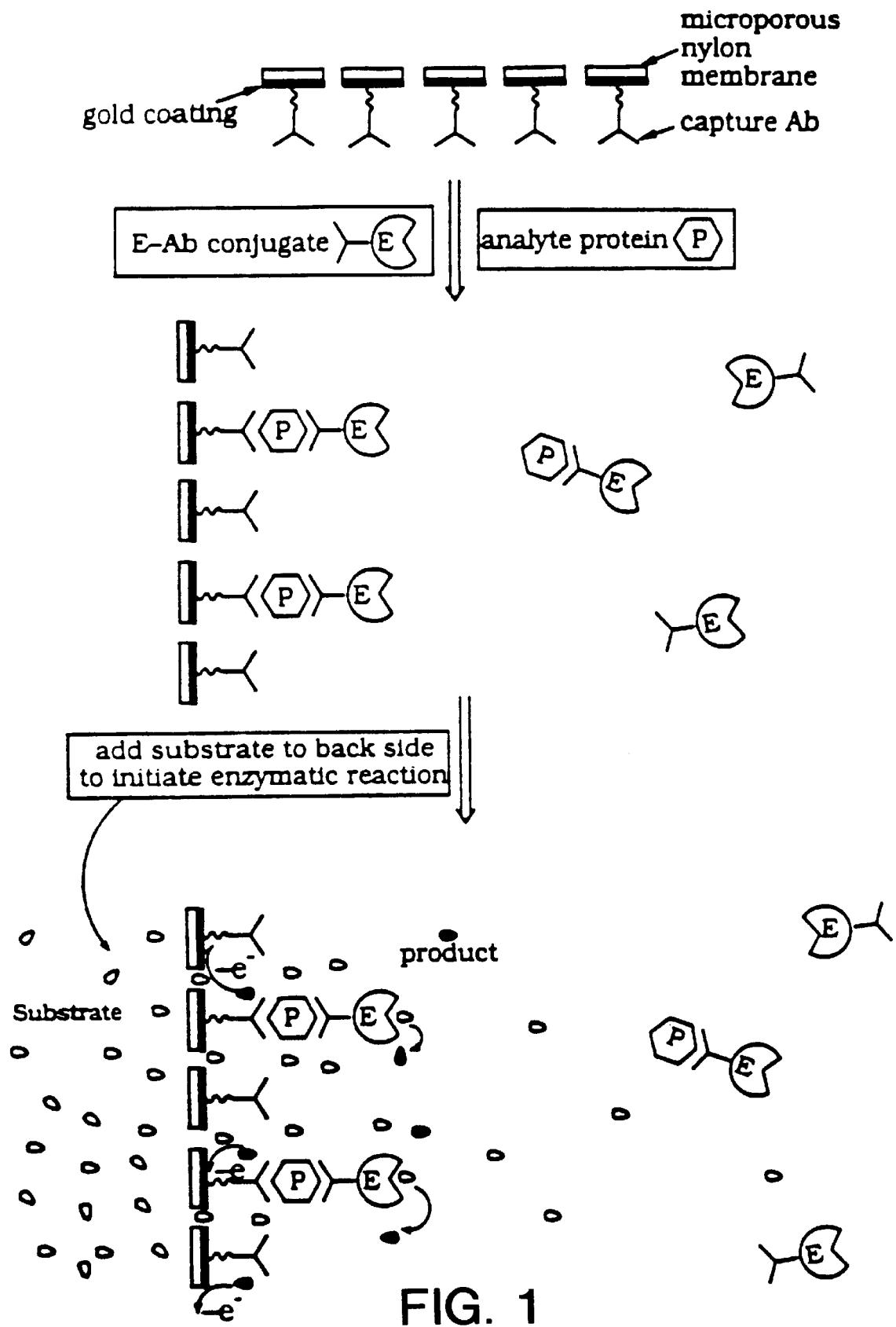
FIG. 1 shows a sequence of steps for the separation-free electrochemical sandwich EIA of the invention.

As illustrated in FIG. 1, samples containing the analyte are incubated concurrently with an enzyme-antibody conjugate, resulting in the capture of the antibody conjugate on the metal-coated, sample side of the microporous membrane support. Examples of analytes that can be detected in this way include hCG (human chorionic gonadotropin, used to confirm pregnancy), prostate-specific antigen (PSA, used to screen for prostate cancer), creatine phosphokinases (isozymes MB, BB and MM; e.g., creatine kinase-MB to detect the occurrence of myocardial infarctions), troponin, myoglobin, light-chain myosin, fibrinogen, thyroid stimulating hormone, follicle stimulating hormone (FSH), hepatitis antigens, and various proteins associated with a wide variety of specific viruses such as the potato virus. For purposes of this invention, the term "analyte" is defined broadly as any protein capable of causing antibody production.

Examples of suitable enzymes and enzyme substrates include a large number of widely varying materials, such as the enzymes and substrates shown in Table I below.

TABLE I

Representative Complementary Enzyme/Substrate Pairs which Involve the Consumption of Production of $O_2$ or $H_2O_2$.[a]

| Entry | Enzyme | Substrate | Electro-active Consumed | Species[b] Produced |
|---|---|---|---|---|
| 1 | uricase | uric acid | $O_2$ | $H_2O_2$ |
| 2 | sarcosine oxidase | sarcosine | $O_2$ | $H_2O_2$ |
| 3 | cholesterol oxidase | cholesterol | $O_2$ | $H_2O_2$ |
| 4 | glycerol-3-phosphate oxidase | glycerol-3-phosphate | $O_2$ | $H_2O_2$ |
| 5 | pyruvate oxidase | pyruvate | $O_2$ | $H_2O_2$ |
| 6 | diaphorase | NADH | $O_2$ | $H_2O_2$ |
| 7 | catalase | $H_2O_2$ | $H_2O_2$, $O_2$ | |
| 8 | L-glutamate oxidase | L-glutamate | $O_2$ | —[d] |
| 9 | bilirubin oxidase | bilirubin | $O_2$ | $H_2O_2$ |
| 10[c] | alkaline phosphatase | BCIP | $O_2$ | $H_2O_2$ |
| 11 | glucose oxidase | glucose | $O_2$ | $H_2O_2$ |

[a]The content of this table is by no means comprehensive with respect to the number of suitable enzyme/substrate combinations or alterative substrates (enzymes) for a given enzyme (substrate). This table serves only to illustrate useful enzymes and their substrates and is not to be construed as limiting the scope and unity of the present invention.
[b]These electroactive species are either consumed or produced or both.
[c]BCIP = Bromochloroindoxyl phosphate. Alternatively, an indoxyl ester (e.g., indoxyl acetate) may be used in conjunction with a esterase enzyme.
[d]Water is formed.

In addition, the following enzyme-substrate pairs are also useful:

(1) arylacrylamidase, which acts on the substrate N-acetyl-p-aminophenol to produce aminophenol;

(2) acetylcholinesterase, which acts on thioacetylcholine to produce thiocholine;

(3) catalase, which consumes $H_2O_2$ to produce $O_2$; and (4) any oxidase that would not produce an interfering species, for example, deamino-oxidase, but not lactic acid oxidase when its native presence in biological materials would interfere with the assay. In a particularly preferred embodiment, alkaline phosphatase is used with aminophenyl phosphate or nitrophenyl phosphate to produce the electrochemical species aminophenol.

However, the preferred substrate is aminophenyl phosphate, which reacts with alkaline phosphatase to produce aminophenol, which can be oxidized at a relatively low positive potential as compared with, for example, nitrophenyl phosphate. By using such a low positive potential, i.e., +0.19 V (vs. Ag/AgCl) for aminophenol, many of the biological interferences that are commonly encountered, such as uric acid, ascorbic acid and the like, do not oxidize appreciably.

Even if such species could be oxidized by the electrode at the very modest anodic potential of +0.19 V, their concentration at the electrode surface can be rapidly depleted during the three-minute period prior to adding substrate from the opposite side to begin the measurement of bound enzyme-antibody conjugate. That is, the large area working electrode can, in principle, be used to pre-electrolyze any interference present in the diffusion layer adjacent to the electrode surface, thus diminishing any background current from these species. As to potential interference from endogenous alkaline phosphatase, the activity of the enzyme-antibody conjugate added in excess to the example significantly exceeds the typical activities of the enzyme found in blood samples.

After a fixed period of incubation, the sandwich is formed. One of the major problems associated with solid phase sandwich assays has been the slow binding kinetics. Because one reagent, the capture antibody, is immobilized, mass transfer of the analyte and the enzyme-labeled antibody conjugate to the surface generally limits the speed of assay. For example, microtiter plate-based solid phase assays often require a one-to-two-hour incubation time for the mixture of analyte and conjugate before the amount of bound enzyme-labeled antibody can be accurately determined.

In general, with a fixed capture antibody solid phase, such as used in the invention, the rate of binding can be increased by using relatively large surface area to bulk sample volume ratios and efficient mixing of the reagent/sample solution in the first chamber. The relatively rough and uneven surface of the metal-coated microporous membrane in combination with mechanical mixing, such as that provided by a stirring device, are thought to help achieve this goal.

Figure 8:
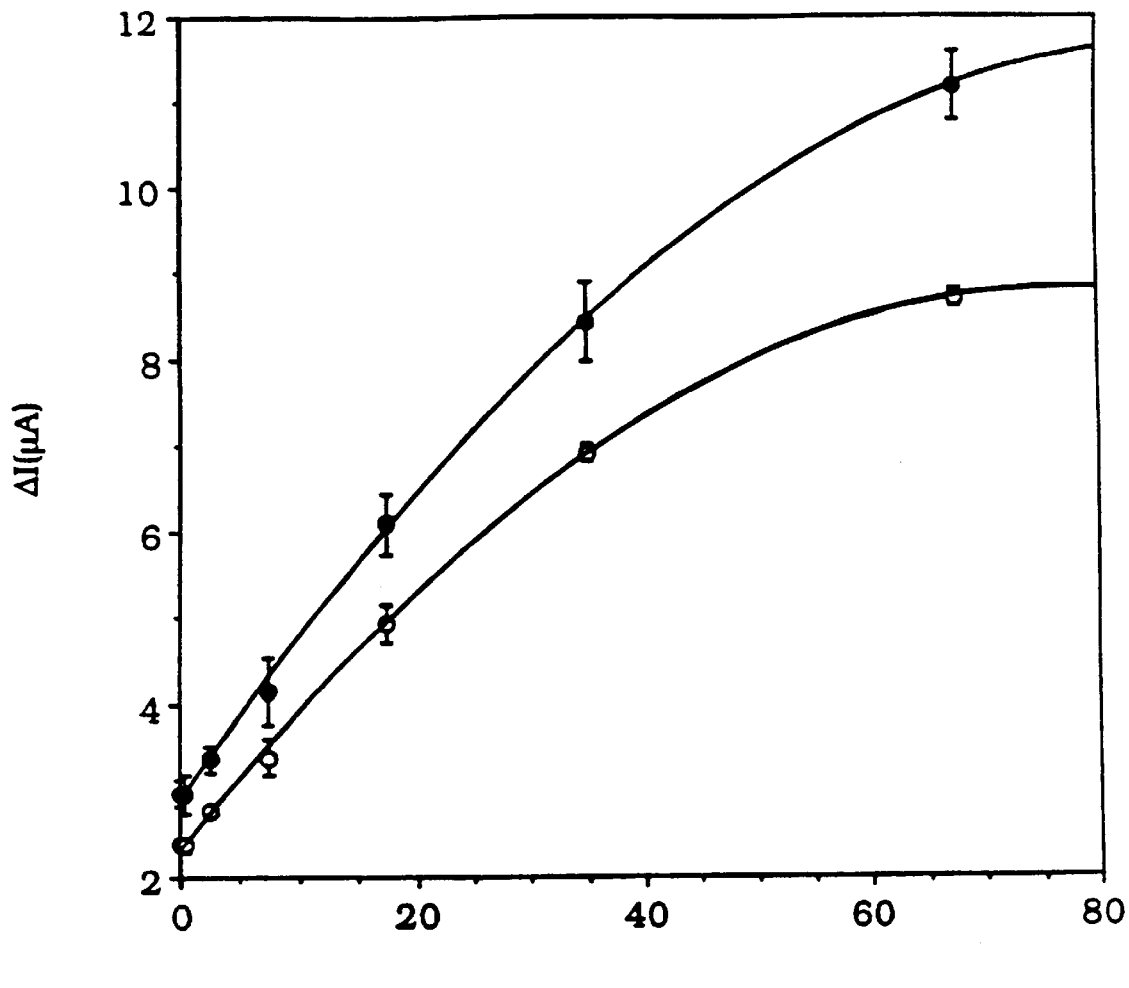
FIG. 8 shows typical calibration curves for hCG in buffer and whole blood.

The concentration of the enzyme-antibody conjugate is an important parameter. As conjugate concentration increases, larger dynamic ranges are achieved, but the detection limit also increases. As shown by FIG. 8, typical calibration curves for hCG in citrate buffer yield a useful linear range from about 0.8 U/l to 40 U/l, preferably from about 2.5 U/l to 40 U/l, using a conjugate concentration of about 0.25 mA or 392 U/l in the sample solution. The detection limit thus achieved is about 0.8 U/l, determined using a signal/noise ratio of 3. This detection range is comparable to a number of reported heterogeneous hCG sandwich assays that require discrete washing steps. Increasing the conjugate concentration to 2.5 mA (3920 U/l enzyme activity) yields a linear response in the range of 25–1000 U/l hCG.

FIG. 8 shows typical calibration curves for hCG in a citrate buffer and whole blood at the following concentrations: 0, 0.5, 2.5, 7.5, 17.5, 35 and 67.5 U/l. Each dosage of hCG was performed two (in buffer) or four times (in whole blood) on individual membranes. The error bars shown in FIG. 8 indicate the range of steady-state currents for each hCG concentration tested, i.e., the change in current from baseline value for different membranes used for each concentration of tested.

The data shown in FIG. 8 suggests that membrane to membrane variations with respect to effective electrode surface area, antibody coverage, etc., are relatively small. These results confirm the potential ability to adapt this methodology to a low-cost, single-use disposable assay format, in which prior calibration of given lots of porous membrane/electrodes could provide adequate accuracy for semi-quantitative analytical purposes.

Figure 9A:
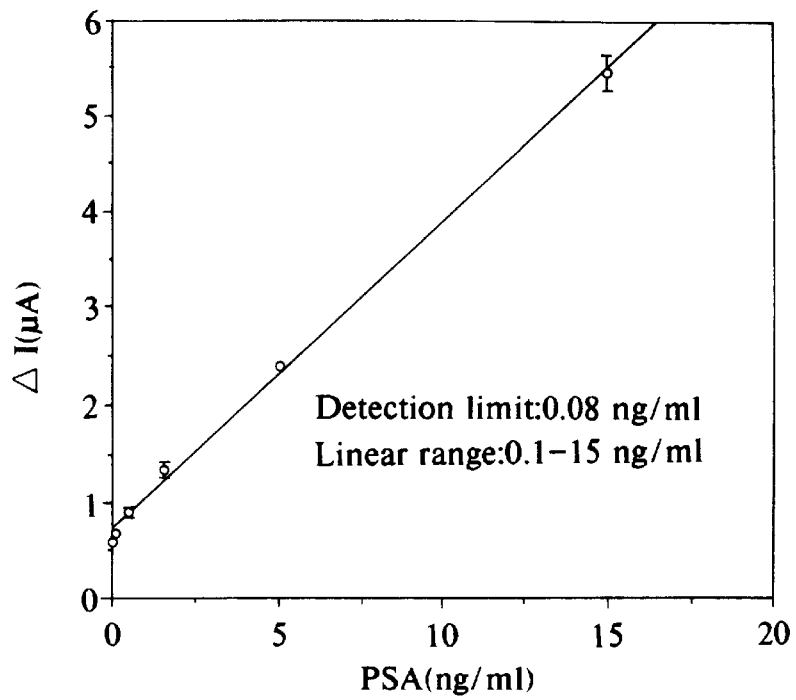
FIG. 9A shows a calibration curve for prostate-specific antigen (PSA) in buffer.
Figure 9B:
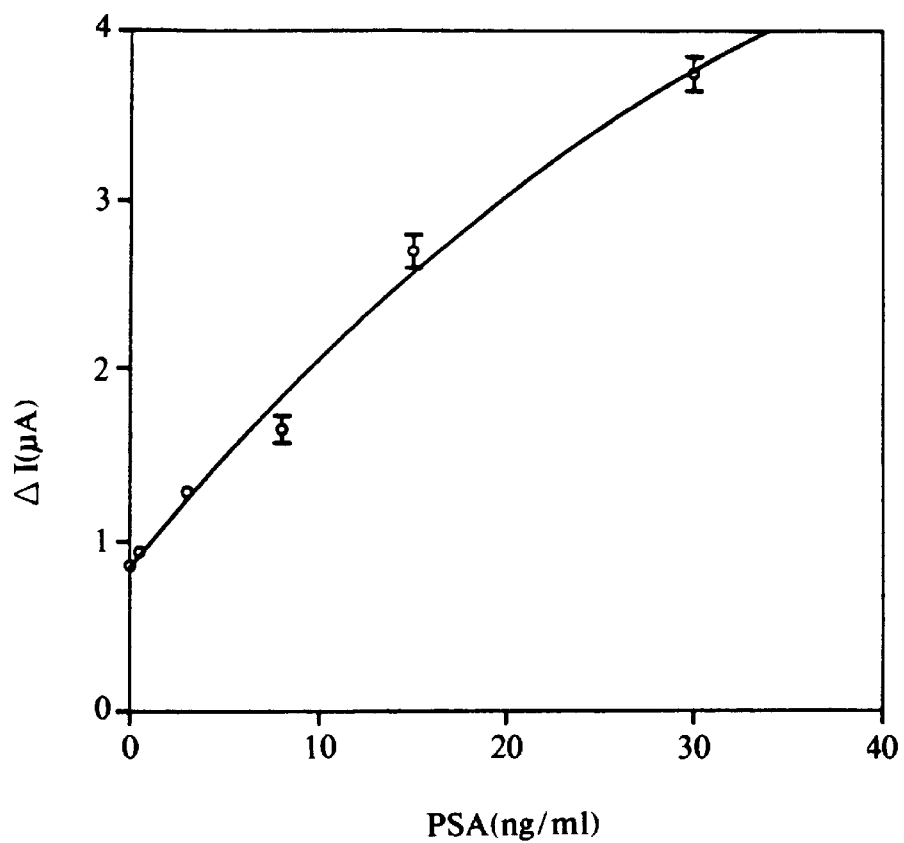
FIG. 9B shows a calibration curve for PSA in pooled female serum.
Figure 9C:
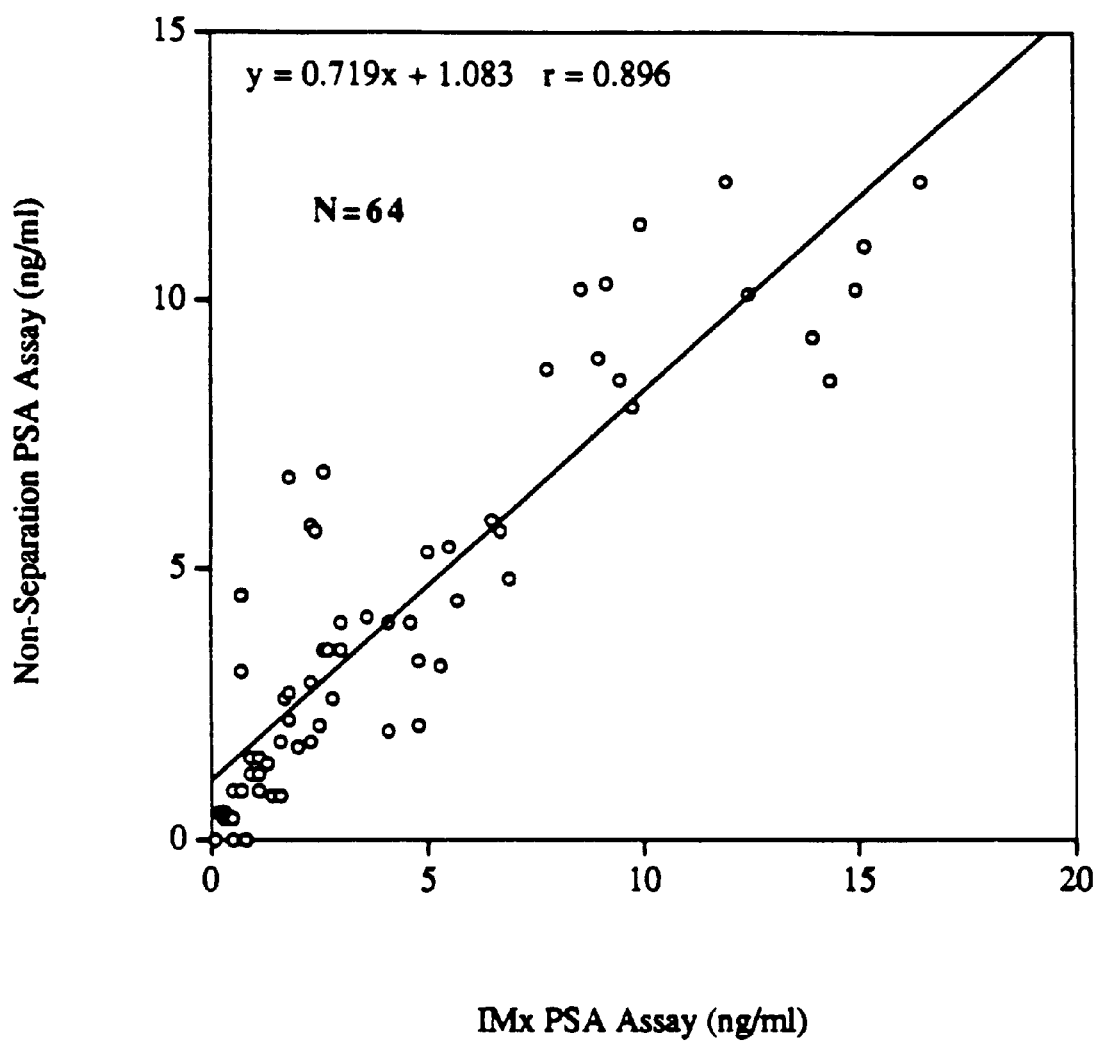
FIG. 9C shows a correlation study of the non-separation method of the invention with a standard IMx PSA assay available from Abbott.
Figure 10:
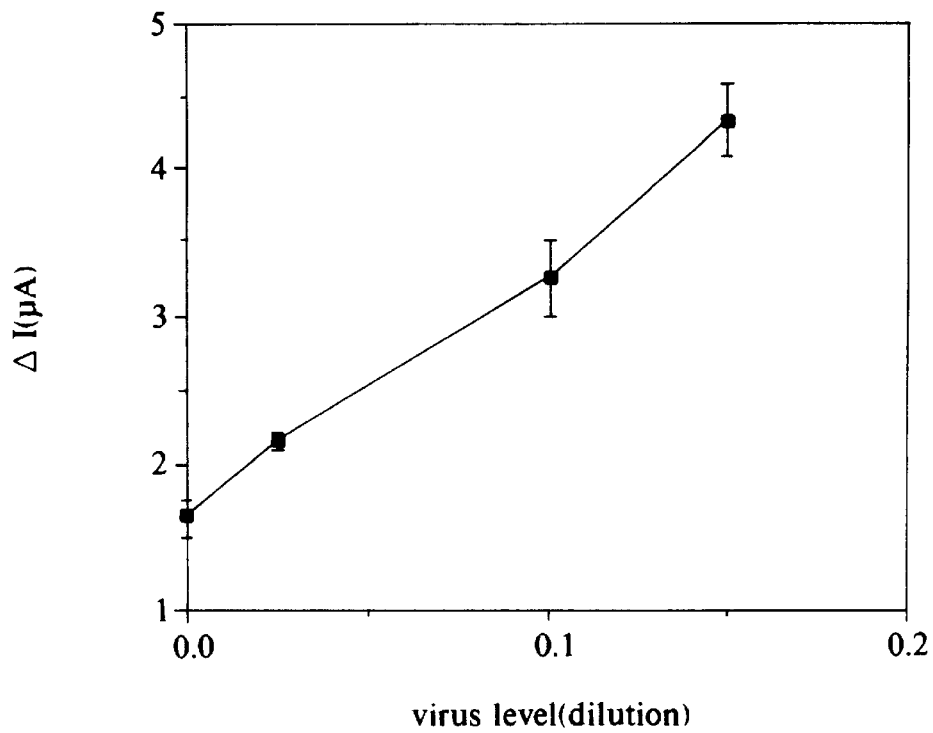
FIG. 10 shows a potato virus A dilution curve.

Similar calibration curves are also provided in FIGS. 9A, 9B and 10 for prostate-specific antigen (PSA) in buffer, PSA in pooled female serum, and the detection of potato virus A protein. In FIG. 9A, the calibration curve was obtained by releasing substrate on the side of the membrane opposite the sample and recording the resulting analytical signal. In this way, a detection limit of about 0.08 ng/ml was achieved over a linear range of about 0.1 to about 15 ng/ml. FIG. 9B depicts the altered calibration curve that is obtained by spiking pooled female serum with different amounts of PSA and incubating the resulting mixture for about 30 minutes, prior to releasing substrate and recording the signal. FIG. 9C demonstrates the correlation of the analytical signal-derived PSA concentration obtained by the assay of the invention (according to the standard curve generated in pooled female serum; FIG. 9B) with a standard, commercially available assay (Abbott IMx PSA Assay).

The surface bound enzyme-labeled antibody is detected by adding a substrate to react with the enzyme produced as a result of binding. For example, when the enzyme is an alkaline phosphatase, a substrate such as aminophenyl phosphate is placed in the second chamber on the other side of the membrane. Adding this substrate initiates the enzymatic reaction. As soon as the substrate diffuses through the membrane, it reacts with any enzyme near the metal surface, i.e., the immuno-bound sandwich, and is converted to an electrochemically detectable product, such as aminophenol.

The concentration of the substrate used in the second chamber on the other side of the microporous membrane can vary widely within a range of about 0.1 to about 200 mg/ml, preferably between about 1 and 20 mg/ml. However, a particularly preferred substrate concentration for the assay is about 5 mg/ml (about 26.5 mM). As a general rule, the substrate concentration should be sufficiently high to yield a detectably large steady-state current for a given amount of conjugated enzyme-antibody. The concentration should also be sufficiently low to maintain the background signal within manageable levels.

Figure 2A:
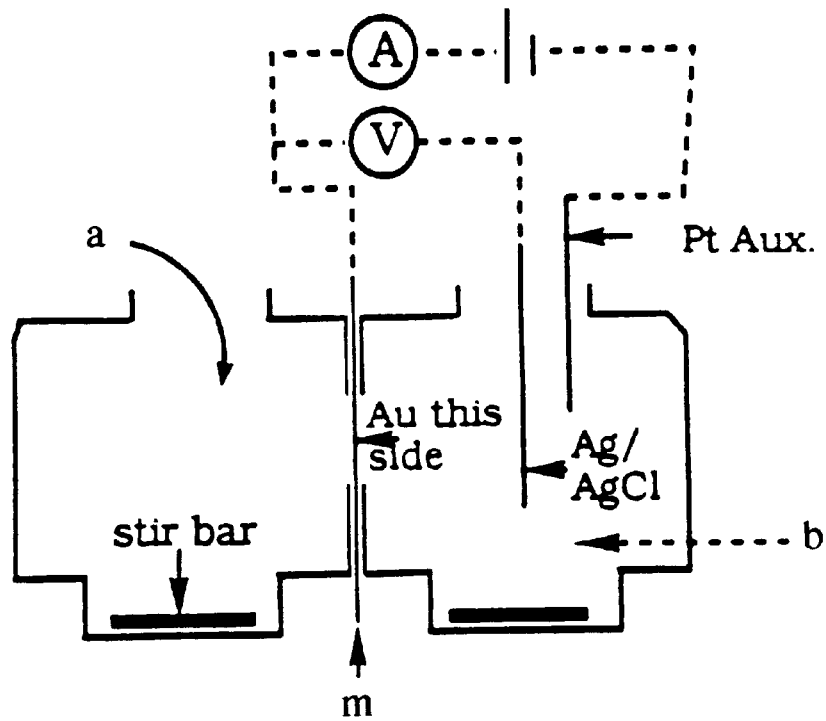
FIG. 2(A) shows a diagram of a diffusion cell arrangement of the invention in which a microporous metal electrode is mounted for non-separation EIA.

Because the solid phase on which the sandwich is formed is also used as an electrochemical detector, as shown in FIG. 2(A), the detectable product formed can be measured as rapidly as it is produced, for example by oxidation at 0.19 V vs. Ag/AgCl when the product is aminophenol. Preferably, the metal-coated microporous membrane is mounted between two chambers of a diffusion cell. During the short period of time immediately after adding the substrate to the second chamber on the other side of the microporous membrane, a relatively small amount of substrate diffuses into the bulk solution in the first chamber on the sample side of the membrane. Thus, only a relatively small product signal originates from the large excess of conjugate present in the bulk solution.

During the initial reaction period, the product of immuno-bound enzyme is concentrated in a small volume adjacent to the surface of the metal electrode. The detectable product concentration in this small volume immediately adjacent to the metal electrode, i.e., the diffusion layer, may be 2–3 orders of magnitude greater than that in the bulk solution.

The concept of adding substrate to a second chamber on the back side, opposite that of the metal conductive layer side, is important for the success of the invention. No useful analytical results are obtained when substrate is added directly to the sample side of the membrane for samples at a number of different pH's (7.4, 9.0 and 10.0). In such cases, the amperometric signal continues to increase until all of the substrate in the bulk solution is consumed by the high concentration of ALP-Ab on the sample side of the membrane. Consequently, no correlation between the amperometric signals and varying levels of hCG can be obtained.

The magnitude of the background signal achieved when no hCG is present in the sample should be equal both at the surface of the electrode and in the bulk solution. The magnitude of the blank signal can, however, be changed depending on the concentration of ALP-Ab used in the assay. Moreover, it is important to recognize that a blank signal can originate from any endogenous alkaline phosphatase present in the blood, or any other endogenous species that can oxidize at the potential applied to the metal electrode.

The proposed method allows for the accurate measurement of surface-bound enzyme-antibody conjugate without first washing away the unbound conjugate in the bulk solution. Therefore, it is possible to perform a separation-free sandwich type assay in both buffer and in whole blood with relatively short assay times and detection limits, as compared to existing heterogeneous EIA methods.

As an additional enhancement in the spatial resolution that can be achieved between surface-bound and bulk enzyme-antibody complex, the pH of the analyte-containing sample in the first chamber can be different from the substrate solution added from the other side of the membrane to the second chamber of the invention.

The physiological pH is around 7.4, and most immunoreactions exhibit optimal binding at about this pH. However, the optimal pH for certain enzymes can be quite different. For example, the optimal pH for alkaline phosphatase activity is about pH 10, as determined electrochemically using aminophenyl phosphate as a substrate. Furthermore, the enzymatic product, 4-aminophenol, is essentially not electrochemically active at pH 7.4. Because it is the phenolate form of this species that is oxidized by the working electrode, a pH of greater than 9.0 is needed to detect amino phenol most efficiently. (The pKb >9.3 for the amino group.)

This paradox can be overcome by using physiological pH on the sample side, for example, 0.01 M citrate at pH 7.4 or a blood sample, while a strong, high pH buffer is used for the substrate solution added to the other side of membrane, e.g., 1.0 M carbonate buffer at pH 10.0. A citrate buffer is preferred for the sample side also because it is a common anti-clotting agent used in blood handling.

Thus, the addition of the substrate solution can set up not only a substrate concentration gradient near the surface of the conductive metal membrane electrode, but also a pH gradient. As a result, the enzymatic activity as well as the electrochemical reactivity of the product is optimized, and the enzyme activity in the bulk solution is significantly reduced. As a specific example, the activity of alkaline phosphatase at pH 7.4 is less than 4% of that at pH 10.00, as determined electrochemically.

Figure 11:
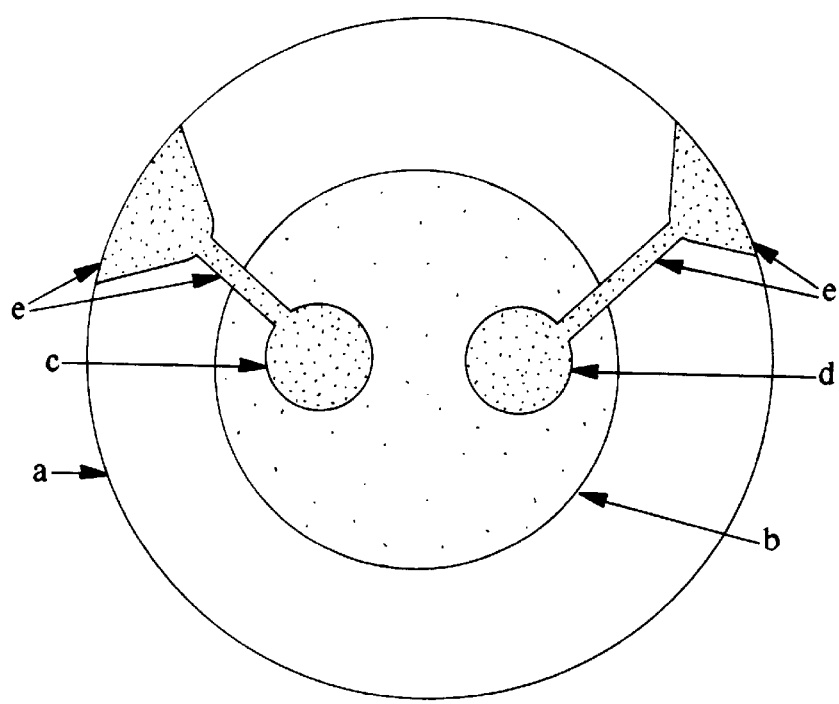
FIG. 11 shows an overview of the membrane arrangement for simultaneous non-separation dual analyte protein assay.

In another embodiment, multiple metal electrodes coated on the same microporous membrane may be used simultaneous multi-analyte measurements, with each electrode having a different anti-analyte antibody immobilized thereon. An example of a useful membrane arrangement for simultaneous non-separation dual analyte protein assay is shown in FIG. 11 with the following elements:

a) microporous nylon membrane having a diameter of about 47 mm;

b) PVC coating on nylon membrane, including a 2 mm-wide metal strip outlet, but not the area intended to carry the metal coating;

c) disc-shaped gold metal coating (diameter of about 3.5 mm) on the microporous nylon membrane having an immobilized anti-PSA capture antibody layer thereon, which serves both as the solid support for the PSA immunoassay and as the metal working electrode for electrochemical detection;

d) disc-shaped gold metal coating (diameter 3.5 mm) having an immobilized anti-hCG capture antibody;

e) gold metal coatings for electrical connections.

Because the signals can be spatially distinguished, assays may be done with multiple enzyme-antibody conjugates but, desirably, are all labeled with the same enzyme, e.g. ALP. The single addition of a common substrate solution from the other side of the microporous membrane is then capable of enabling the measurement of surface-bound enzyme-antibody conjugates at each metal electrode in the array.

Figure 12:
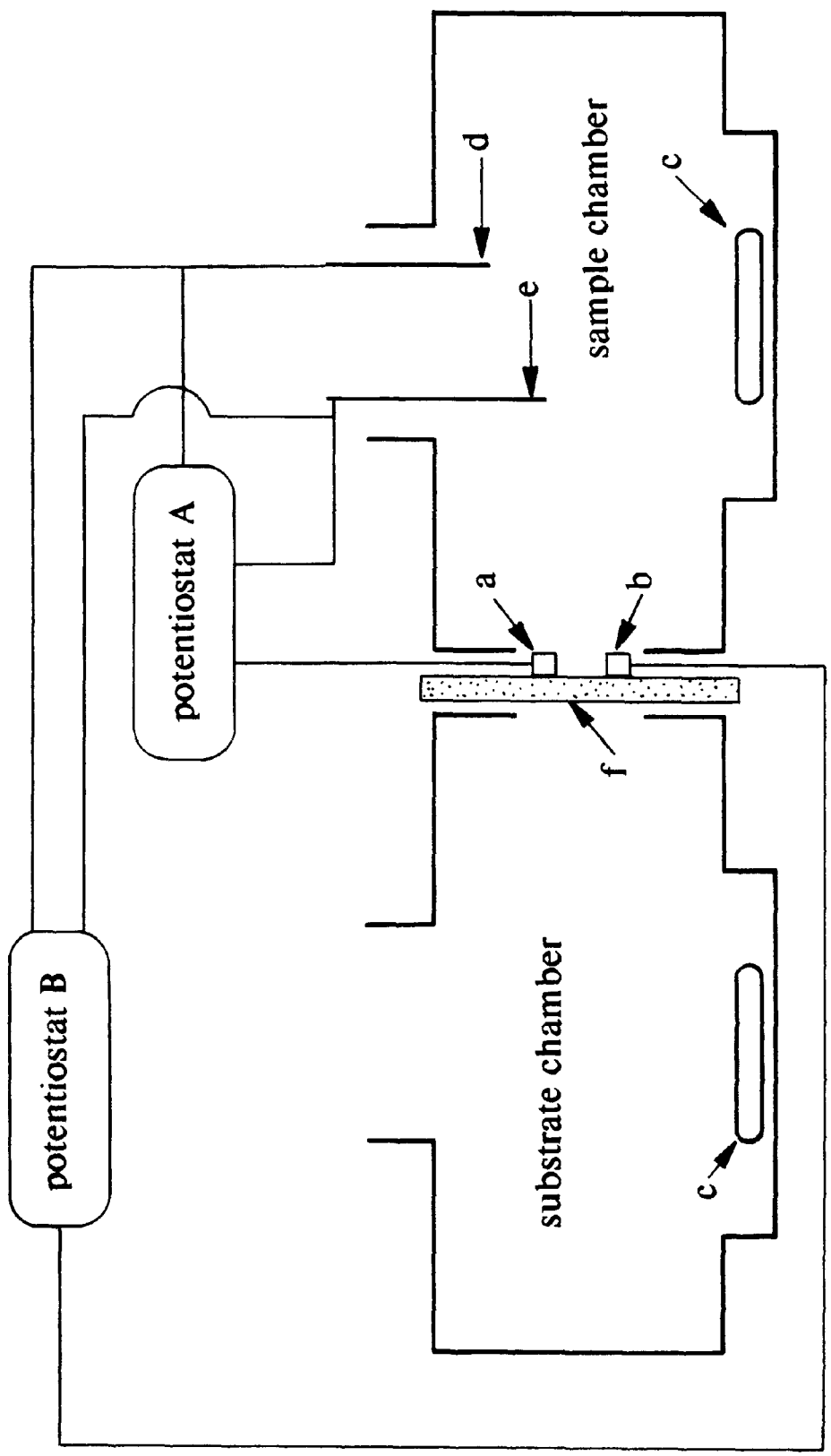
FIG. 12 shows an apparatus for simultaneous dual analyte protein assay.

A particularly preferred apparatus for simultaneous dual analyte protein assay is illustrated in FIG. 12, and has the following components:

a) gold working electrode having thereon a layer of immobilized anti-PSA capture antibody;

b) gold working electrode having thereon a layer of immobilized anti-hCG capture antibody;

c) magnetic stirring bars;

d) common platinum counter-electrode for both (a) and (b);

e) common Ag/AgCl reference electrode for both (a) and (b);

f) microporous nylon membrane coated with gold metal discs (a) and (b) and mounted between the two diffusion chambers (substrate chamber and sample chamber).

Figure 13:
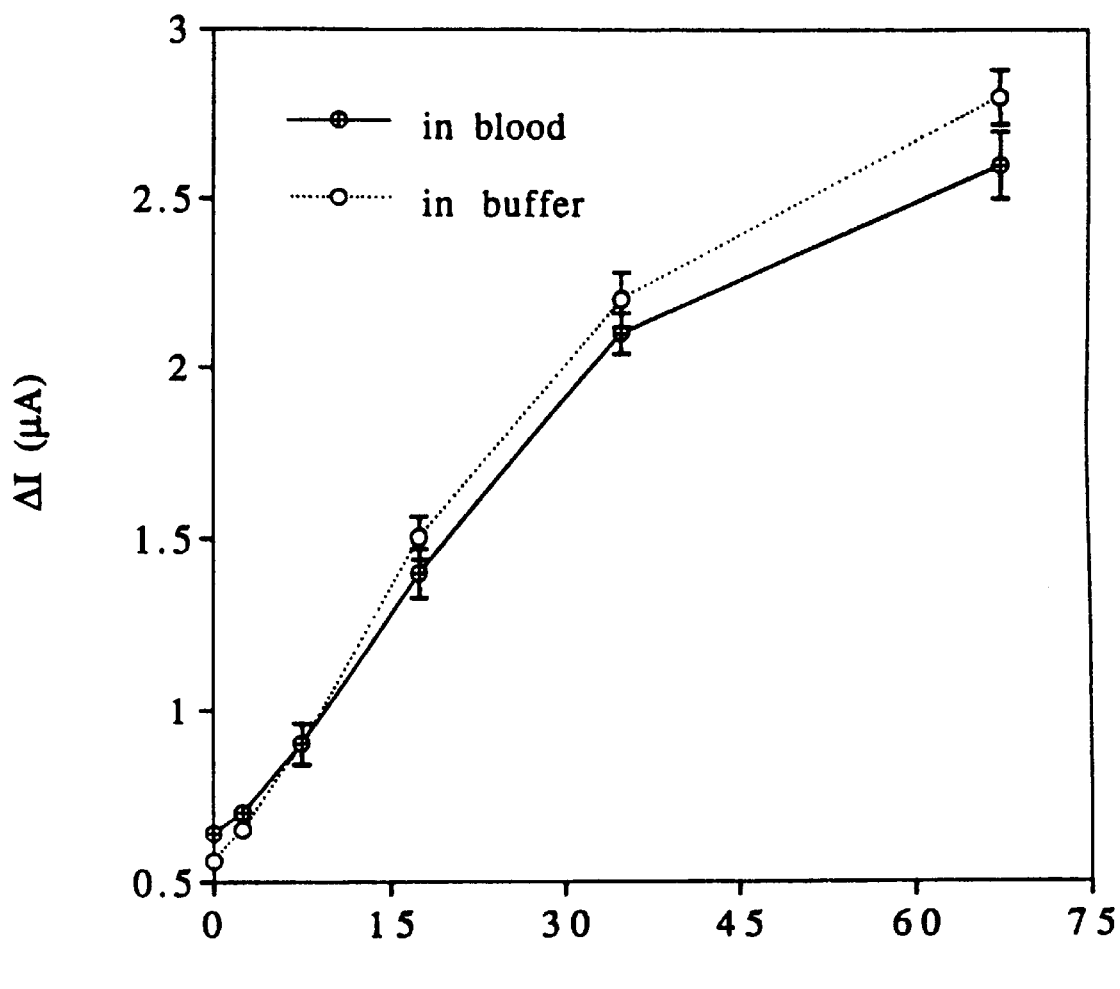
FIG. 13 shows a calibration curve for hCG in buffer and in blood as a result of a dual analyte protein assay of PSA and hCG.
Figure 14:
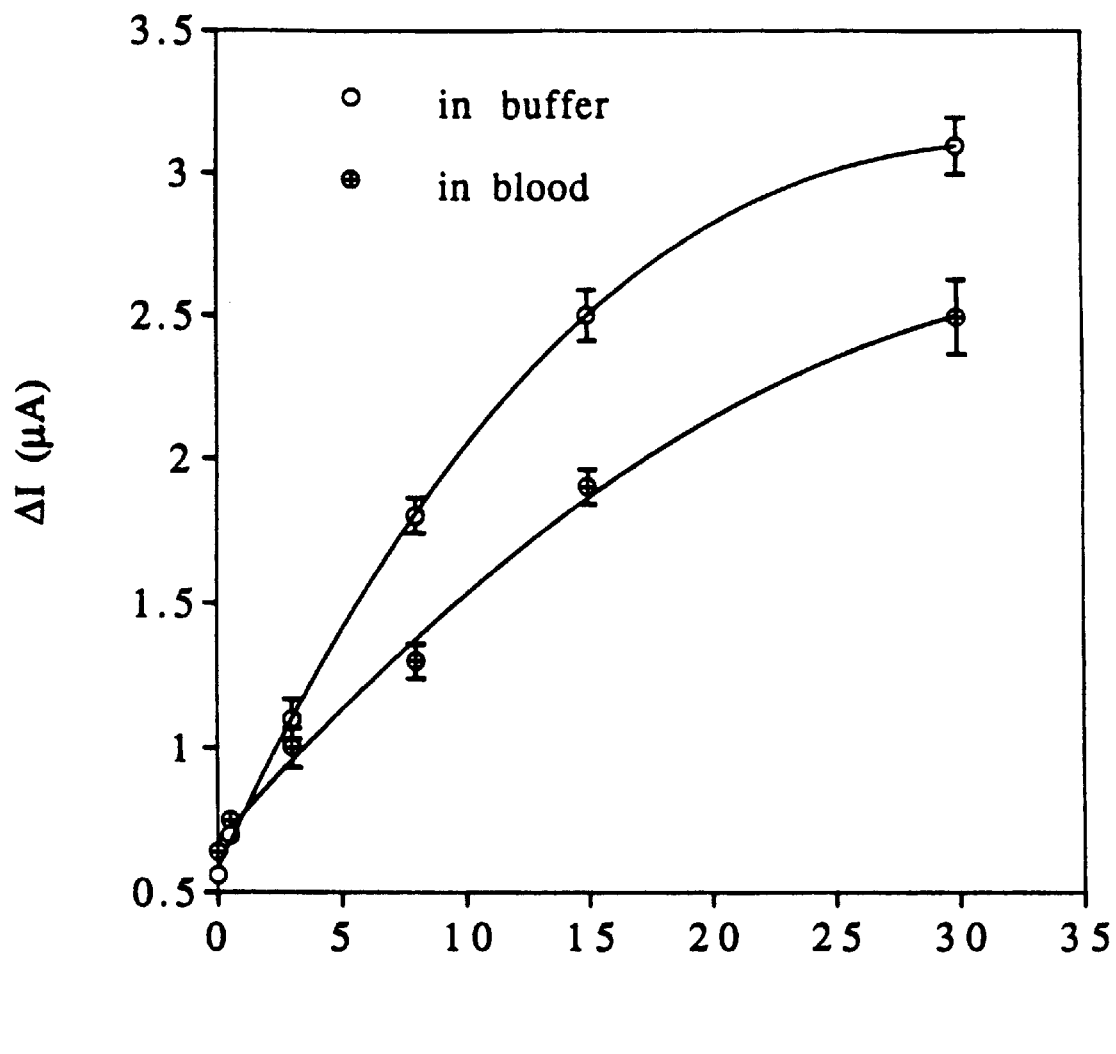
FIG. 14 shows a calibration curve for PSA in buffer and in blood as a result of a dual analyte protein assay of PSA and hCG.

FIG. 13 is a calibration curve obtained for the protein hCG obtained in buffer and in blood in the above-described simultaneous dual non-separation assay for PSA and hCG; FIG. 14 is the corresponding calibration curve obtained for PSA in both buffer and blood in the dual non-separation assay.

Figure 15:
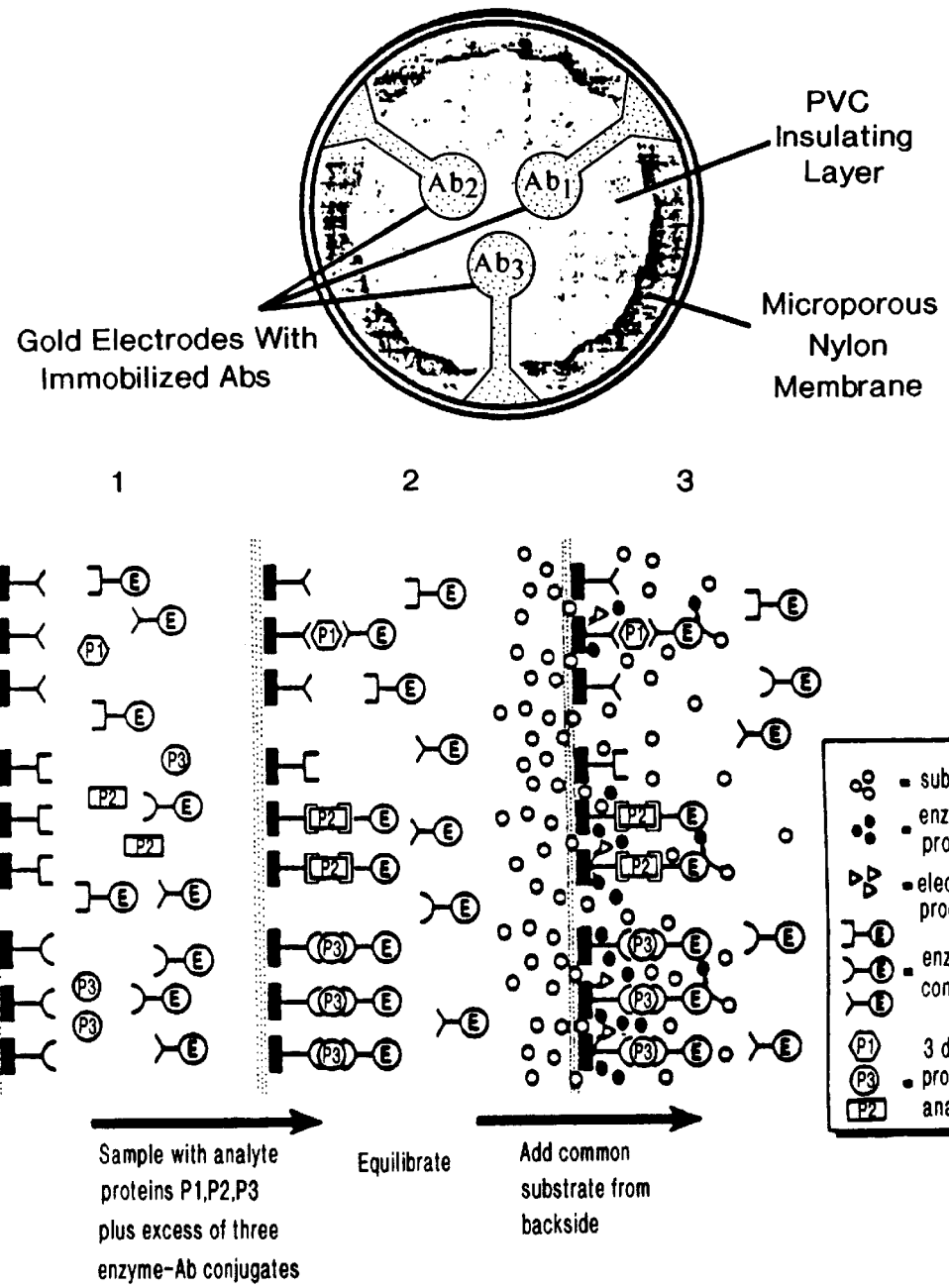
FIG. 15 shows how simultaneous multiple protein measurements can be carried out with a single microporous membrane coated with an array of gold electrodes and different capture antibodies.

FIG. 15 is a schematic representation of how simultaneous multiple protein, non-separation electrochemical immunoassay ("NEEIA") measurements can be carried out with a single microporous membrane coated with an array of three gold metal electrodes and different capture antibodies. A particularly preferred group of analytes to be detected by such a panel of electrodes is a group of analytes valuable in providing diagnostic information regarding cardiac ailments, e.g., two or more of creatine phosphokinase-MB, troponin, myoglobin, fibrinogen, and/or light-chain myosin.

The invention will be further clarified by the following examples, which are intended to be purely illustrative of the invention.

EXAMPLE 1

Preparation of Microporous Gold Membrane

Microporous nylon membranes having a pore size of 0.2 $\mu$m, which had been purchased from Gelman Science (Ann Arbor, Mich.) under the trade name Nylaflo, were cut in circles with o.d. of 47 mm. The circular membranes were placed under a mask having a 6 mm hole at the center and a 2 mm wide outlet strip for electrical connection purposes and then coated with gold for 200 seconds with a Denton Vacuum Desk-11 Cold Sputter-Etch Unit. This produced a disk-shaped gold electrode at the center of the membrane having an outer diameter of 6 mm and a thickness of about 600 Angstroms. Scanning electron microscopy of the resulting membranes was carried out on a Hitachi S-570 instrument (under Grant #BSR-83-14092 from NSF). With a gold layer thickness of about 600 Angstroms, the resulting gold coated membrane was shown to still be completely microporous, with an average pore size estimated to be 0.2 $\mu$m. The scanning electron micrograph also showed that the coated areas of gold were continuously connected with each other to make the entire 6-mm-diameter disk an integrated electrode.

EXAMPLE 2

Immobilization of Capture Antibody and Electrode Formation

The gold-coated membranes of Example 1 were placed in 2% (w/w) thioctic acid in absolute ethanol for 24 hours with shaking. The membranes were then rinsed twice with ethanol and dried. They were then immersed into 1% (w/w) EDC in anhydrous acetonitrile for five hours to activate the free carboxyl groups of the thioctic acid and form an O-acyl-urea intermediate.

Figure 2B:
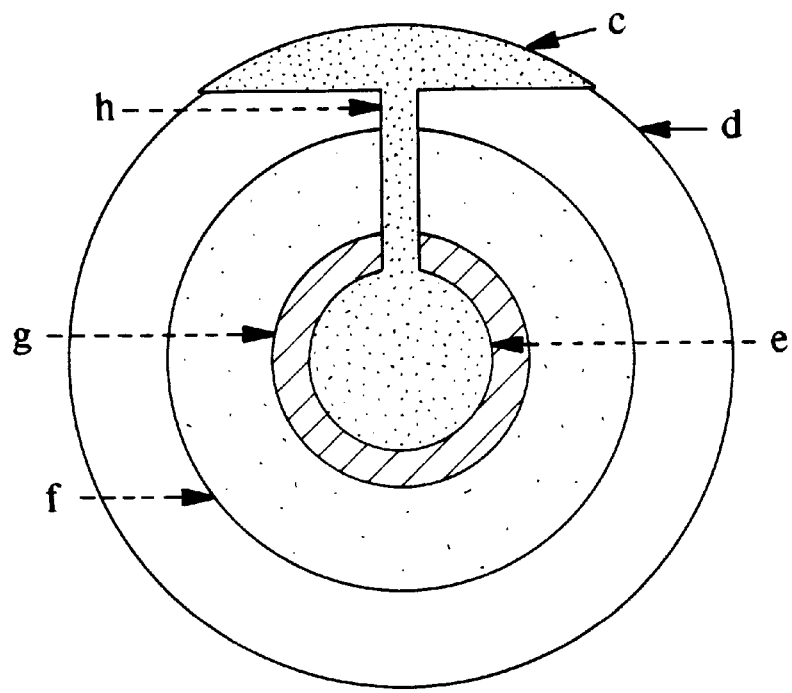
FIG. 2(B) shows an expanded view of a microporous membrane configuration of the invention.

After rinsing the membranes twice with acetonitrile, a silver wire was fixed onto the outer edge of the narrow (2 mm) gold lead with silver epoxy for electrical connection to the potentiostat, as illustrated in FIG. 2(B). FIG. 2(B) provides an expanded view of a preferred microporous membrane configuration, where (c) is a gold metal coating for establishing an electronic connection via clip or solder; (d) refers to the microporous membrane; (e) represents the disc-shaped gold metal coating with an antibody immobilized, forming a working electrode; (f) refers to a coating of an insulator such as polyvinyl chloride; (g) designates the open hole between diffusion cells; and (h) points out a gold metal coating outlet.

A layer of PVC (33% PVC, 67% Bis (2-ethylhexyl) sebecate (both w/w %) dissolved in THF (1:6 w/v) was cast around the center disc electrode, including over the narrow gold lead outlets. The 6 mm disc shaped gold electrode was left untouched in the center.

Thirty $\mu$l of monoclonal anti-hCG capture antibody (Ab, 2 mg/ml in 0.1 M borate buffer, pH 8.75) (obtained from Hybritech Inc., La Jolla, Calif.), was dropped on the exposed microporous gold for immobilization. The membranes were then put into a refrigerator for further reaction and storage. After 24 hours, the immobilization process was complete, and the membranes were soaked in 0.1 M borate buffer, pH 8.75 containing 5% (v/v) ethanolamine to block any unreacted, but still active, O-acyl-urea intermediates. The membranes were rinsed with water and mounted in the diffusion cell of the invention to perform non-separation sandwich assays. FIG. 2B illustrates an expanded view of the final microporous gold electrode-microporous membrane.

EXAMPLE 3

Characterization of Microporous Gold Electrodes

After antibody immobilization and electrode formation, an individual membrane was mounted between the two diffusion cell chambers of the device of the invention to test the electrochemical response of the membrane to 4-aminophenol, the product of the reaction catalyzed by alkaline phosphatase (ALP) when using aminophenyl phosphate as the substrate. The arrangement of the two chambers of the device is illustrated in FIG. 2(A), where (a) represents the addition of substrate to initiate the enzymatic reaction; (b) designates the buffer or whole blood in which the analyte protein and enzyme-antibody conjugate are incubated with capture antibody immobilized on the gold surface; and (m) refers to a gold metal-coated microporous membrane.

The sample side of the diffusion cell, which is in contact with the gold side of the membrane electrode, was filled with 2.0 ml of 0.1 M carbonate buffer, pH 10.0. Using a BAS CV-27 potentiostat in a three-electrode mode at 0.19 V vs. Ag/AgCl reference electrode, with a large platinum wire as the auxiliary electrode to perform amperometric measurements, a potential of 0.19 V vs. Ag/AgCl was applied to the gold coating.

4-Aminophenyl phosphate was synthesized by the reduction of 4-nitrophenyl phosphate in accordance with a previously reported procedure, Christie et al., *Anal. Chim. Acta* 21, 257 (1992), the disclosure of which is hereby incorporated by reference. A solution of 4-aminophenol in ethanol was added to the stirred buffer solution in varying aliquots. The steady-state current observed following each change in product concentration was recorded on a Fisher series 5000 chart recorder. For comparison purposes, the amperometric response to 4-aminophenol of gold-coated membrane electrodes that had not been treated with antibody or thioctic acid were also evaluated.

Figure 5A:
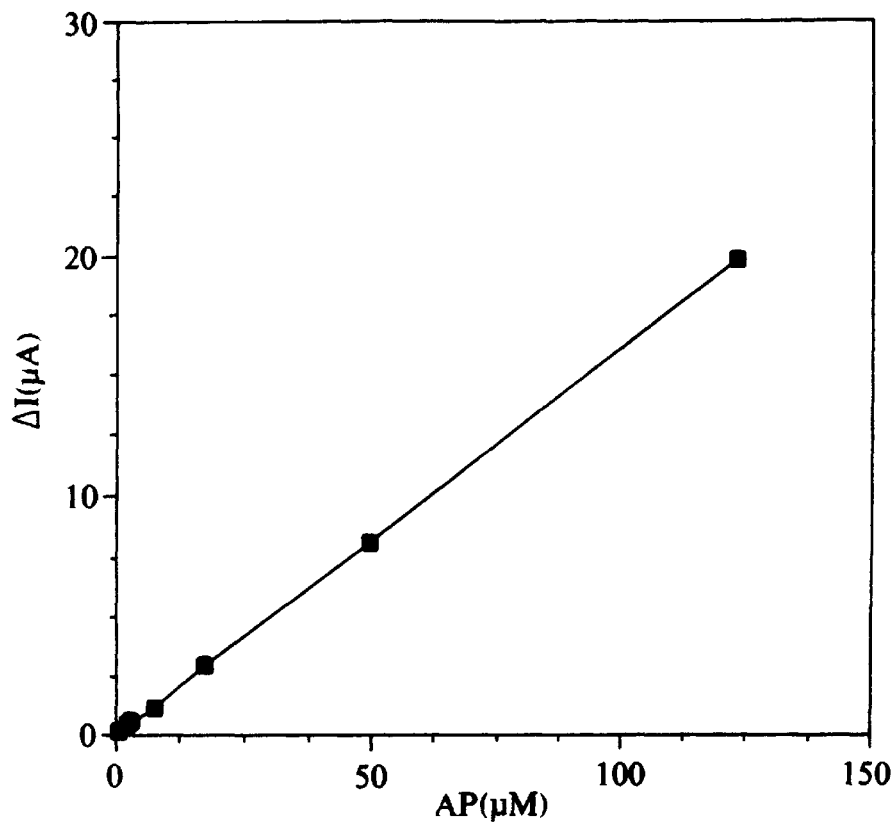
FIG. 5 shows the amperometric response of a microporous gold electrode toward varying concentrations of the electrochemically detectable species aminophenol at 0.19 V vs. Ag/AgCl.
Figure 5B:
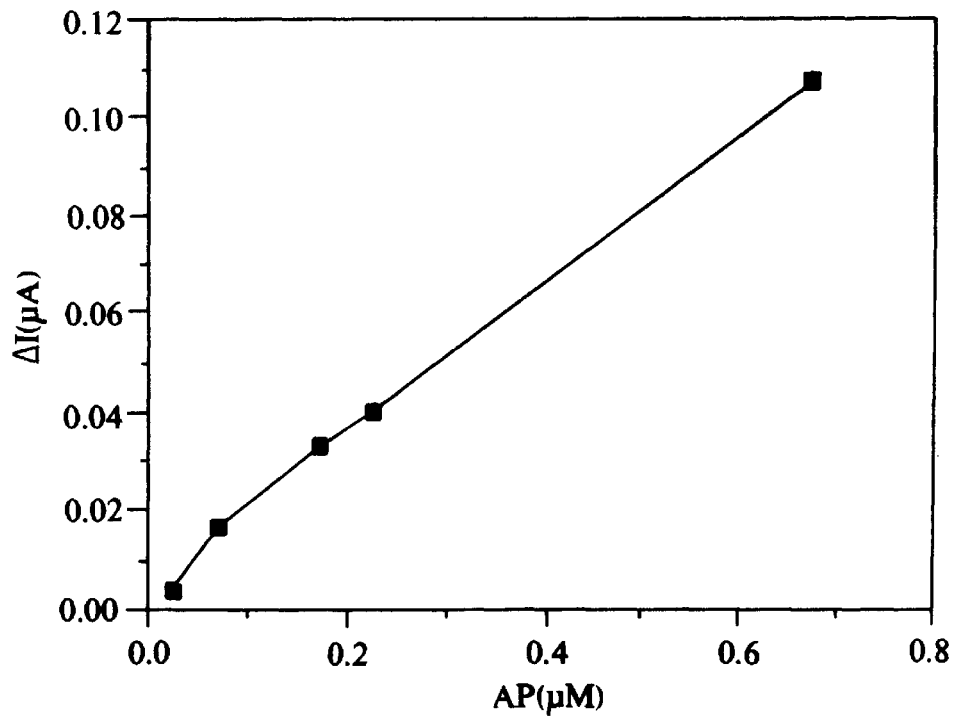

FIG. 5 illustrates the ability to use this gold-coated microporous membrane as a working electrode for the measurement of 4-aminophenol, the enzymatic product of alkaline phosphatase activity on the substrate 4-aminophenyl phosphate. The amount of antibody immobilized (191 $\mu g/cm^2$ of apparent geometric area) was determined by using a Pierce BCA protein assay kit to quantitate the amount of anti-hCG remaining after the immobilization step (including protein recovered after washing the membrane to elute all non-covalently attached antibody). The gold electrode treated with immobilized antibody retained its ability to exhibit linear amperometric response over a wide range of 4-aminophenol concentrations. The detection limit of the microporous membrane electrode toward reagent grade 4-aminophenol in the direct amperometric measurement mode (at 0.19 V vs. Ag/AgCl) was approximately $10^{-7}$ M. In FIG. 5, each data point represents the average of three measurements performed with porous electrodes on which monoclonal anti-hCG antibodies were immobilized.

The responses of several bare microporous gold electrodes to 4-aminophenol, without immobilized antibody, were also examined. It was found that the bare gold yielded similar linear responses, but the steady-state current for a given concentration of 4-aminophenol was about twice that of the gold electrodes with immobilized antibody. Clearly, immobilization reduced the electrochemically available surface area (calculated to be on the order of 0.55 $cm^2$ for the antibody-immobilized porous electrode based on chronoamperometric measurement of the oxidation of ferrocyanide at 0.8 V vs. Ag/AgCl) and/or the kinetics of electron transfer at the gold/solution interface.

Nevertheless, even after antibody immobilization, the gold electrode surface was still accessible to 4-aminophenol. After the gold surface was treated with thioctic acid and the residual carboxyl groups were capped with ethanolamine, the environment several angstroms away from the gold surface was neutral, making it possible for neutral and/or negatively charged 4-aminophenol to have access to the gold surface. Although not wishing to be limited to any particular mechanism, it was speculated that this access may be due to electron tunneling or defects in the monolayer of thioctic acid, particularly on the polycrystalline gold electrode described above.

The kinetics of the immunobinding of hCG and the enzyme-antibody conjugate (ALP-Ab, alkaline phosphatase-anti-hCG antibody conjugate from Hybritech Inc., La Jolla Calif.) with capture anti-hCG antibody immobilized on the surface of the microporous gold electrode were studied in both buffer solution and whole blood. About 35 U/l hCG (human chorionic gonadotropin from Sigma, Saint Louis, Mo.) (one unit corresponding to about 200 ng of protein) were incubated together with 0.25 milliabsorbance (mA) of ALP-Ab conjugate in 2 ml of 0.01 M, citrate buffer, pH 7.4, or human blood. (0.25 mA is equivalent to 392 U/l enzyme activity as determined by calorimetric means in 1 M carbonate buffer, pH 10, using p-nitrophenyl phosphate as a substrate.) Human blood was regenerated by mixing 40% red blood cells with 60% compatible plasma. The incubation mixture was mixed in the first chamber for varying periods of time before stirring was stopped and substrate solution was added to the second chamber on the opposite side of the microporous membrane support.

Figure 6:
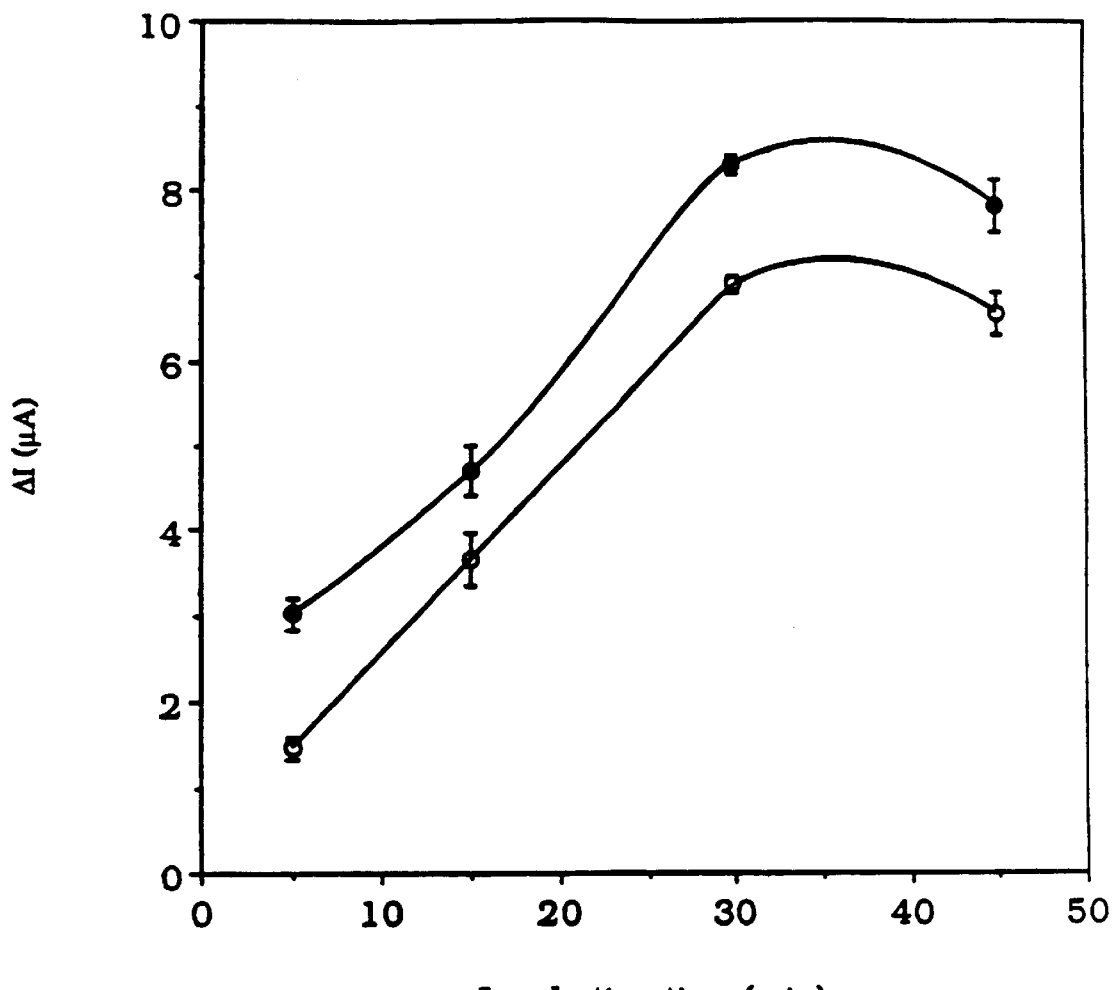
FIG. 6 shows a kinetic curve for sandwich-type immunobinding in buffer and in whole blood.
Figure 7:
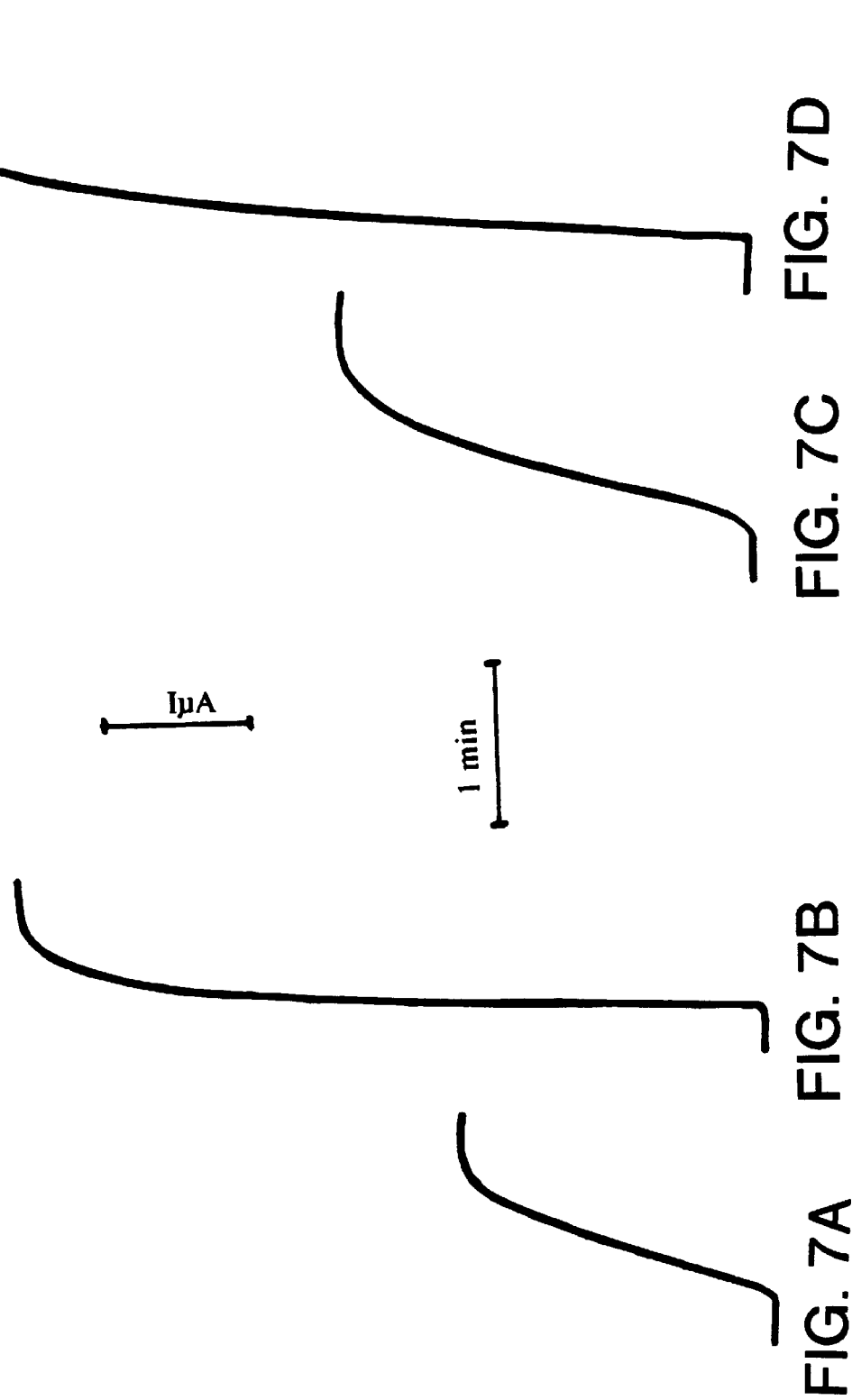
FIGS. 7(A)–7(D) show typical dynamic response curves for the separation-free electrochemical sandwich type EIA of the invention in buffer and in whole blood.

As the results show in FIG. 6, for an analyte concentration of 35 U/l, optimal sandwich formation occurred after about 30 minutes of incubation. This was true for both aqueous and whole blood samples. (Each data point in FIG. 6 is the average (plus range) of two measurements using two different membranes.) By design of smaller diffusion cell arrangements having even higher electrode surface area to bulk sample volume ratios, it should be possible to reduce this 30-minute pre-incubation time even further. However, even a 30-minute pre-incubation time represents an improvement in efficiency when compared to the time and additional effort required to separate serum from whole blood.

There was observed a background signal when no hCG was present, thought to be primarily due to the concentration of unbound enzyme-antibody conjugate in the assay mixture, which was equivalent at the surface of the electrode and in the bulk solution. This blank signal changed, depending on the concentration of the enzyme-antibody conjugate used in the assay. The source of the blank signal in whole blood could have originated from any endogenous alkaline phosphatase present in the blood, as well as any endogenous species that could oxidize at the potential applied to the gold electrode.

EXAMPLE 4

Non-Separation EIA's

To enhance the spatial resolution of surface-bound ALP-Ab conjugate from the bulk unbound reagent, buffers of different pH were used on the two sides of microporous membrane support. On the sample side of the permeable membrane was placed a 0.01 M citrate buffer, pH 7.4, with 1 mM $MgCl_2$ and 1% Heat Shock BSA. To obtain an hCG analyte calibration curve, different doses of the hCG together with the ALP-Ab conjugate were added to the sample side containing the citrate buffer to make the final volume of liquid on the sample side 2.0 ml. The final concentration of ALP-Ab conjugate equaled 0.25 mA/2 ml.

This sample mixture was incubated in the sample side, first chamber for 27 minutes with stirring. The stirring was then stopped, and a potential of 0.19 V vs. Ag/AgCl was applied to the gold electrode.

After allowing 3 minutes to attain a steady-state baseline current, two ml of a 26.5 mM solution of the substrate 4-aminophenyl phosphate, which had been prepared in 1.0 M carbonate buffer (pH 10.0), was added to the second chamber on the opposite side of the membrane to initiate the measurement of surface-bound ALP-Ab conjugate. A steady-state current was achieved within about 50 seconds for all assays, with the actual length of time depending on the hCG concentration being present. The more hCG that was present, the faster was the response. The current-time course was monitored on a strip-chart recorder. The change in current from baseline to steady-state was plotted against different doses of hCG to obtain a calibration curve for hCG.

In contrast to other sandwich EIA's, the time required to obtain the analytic signal after the immunobinding step was quite rapid. FIGS. 7(A)–7(D) show the dynamic amperometric response of gold microporous membranes after being equilibrated with a sample and the ALP-Ab conjugate for 30 minutes, followed by addition of 2 ml of 26.5 mM aminophenyl phosphate to the second chamber on the back side of the porous membrane. The samples used to obtain the four curves depicted in FIGS. 7(A)–7(D) are as follows:

(A) 0 hCG in buffer;
(B) 17.5 U.l hCG in buffer;
(C) 0 hCG in whole blood; and
(D) 17.5 U.l hCG in whole blood.

A steady-state amperometric response was achieved in about one minute. The magnitude of the background signal when there is no hCG reflected primarily the concentration of unbound ALP-Ab in the assay mixture, which is equivalent at the surface of the electrode and in the bulk solution.

To demonstrate an assay of whole blood, human blood samples spiked with varying levels of hCG were used as samples in the assay. The final volume of the blood was 2.0 ml, in which the human blood accounted for no less than 93% (v/v) of the total volume, i.e., extraneous reagents and hCG standards constituted less than 7% (v/v). Otherwise, the assays of blood samples were the same as the assays of analyte in a buffer solution. The blood samples were incubated together with the ALP-Ab conjugate for 27 minutes in the first chamber on the sample side of the membrane and achieved a steady-state amperometric response when substrate was added to the second chamber in about one minute. As shown in FIG. 8, the detection limit, dynamic range, and reproducibility for the in situ detection of hCG in whole blood were comparable to that in buffer solution. Detection limits were only slightly higher (2.5 U/l, using S/N=3) due to the larger standard deviation of the blank signal in the case of blood measurement. This is comparable to most heterogeneous hCG assays that require multiple washing steps and are performed with serum, not whole blood samples.

With regard to potential interference from endogenous alkaline phosphatase, the activity of the AlP-Ab conjugate added in excess to the sample far exceeded the typical activities of the enzyme found in blood samples. Although metal electrodes in contact with biological samples are known to foul, presumably due to the adsorption of proteins and the like, this did not happen in the method, device and cassette of the invention.

It should be noted that the response in blood samples was somewhat larger than that in the aqueous buffer (for a given concentration of hCG). This is though to be due to slight differences in the binding affinity and/or nonspecific absorption of the ALP-Ab conjugate to the capture antibody immobilized on the porous metal, i.e., compared to non-physiological conditions in 0.01 M citrate buffer. Further, for the eventual practical use of the assay scheme in the invention for whole blood measurements, the hematocrit of the blood would be a variable that will control the concentration detected. All current sandwich EIA's for blood proteins use only serum or plasma as the samples. In any correlation study, the values measured in a whole blood sample would have to be corrected for what fraction of the total sample volume is due to red blood cells. Nonetheless, the method of the invention provides a valuable way to screen for elevated levels of a given protein in whole blood, e.g., CPK-MB, hCG or PSA, for rapid diagnostic purposes.

In summary, a new method for performing separation-free sandwich-type EIA's for proteins has been introduced using the cassette and/or the device of the invention in the method of the invention. The EIA is preferably performed by an electrochemical detection system that enables preferential measurement of surface-bound enzyme-labeled antibody relative to the excess enzyme-labeled reagent in the bulk sample solution. The EIA method of the invention functions well both in buffer and in complex biological media.

I claim:

1. A method for performing a non-separation, enzyme sandwich immunoassay for at least one predetermined analyte comprising:
  (a) providing a reaction vessel divided into first and second chambers by a microporous membrane support, such that
    (i) said fist chamber is capable of containing at least a first enzyme-labeled antibody, wherein said first enzyme-labeled antibody specifically binds to said first analyte and said labeling enzyme is capable of reacting with a substrate to produce an electrochemically detectable product,
    (ii) said second chamber is capable of containing said substrate, and
    (iii) a side of said separating microporous membrane support facing said first chamber is coated with
      (1) a conductive metal layer and
      (2) at least a first capture antibody layer immobilized over said conductive metal layer in at least a first spatially distinct area of said microporous membrane support,
  wherein said conductive metal layer functions as an electrode to detect, directly or indirectly, said electrochemically detectable product and said microporous membrane support is permeable to said substrate;
  (b) adding a sample to be tested to said first chamber to contact said capture antibody layer with any said at least one predetermined analyte in said sample;
  (c) adding said at least a first enzyme-labeled antibody to said first chamber to bind to any said at least one predetermined analyte bound to said capture antibody layer;
  (d) adding said substrate to said second chamber such that it diffuses through said microporous membrane support and react with said labeling enzyme to produce said electrochemically detectable product,
  (e) determining said electrochemically detectable product at said conductive metal layer to determine the presence or amount of said at least one predetermined analyte in said test sample; and
wherein the pH of the analyte-containing sample in the first chamber is different from the pH of the substrate solution added to the second chamber, such that a pH gradient is created near the conductive metal layer, and wherein either the activity of said labeling enzyme, or the activity of said electrochemically detectable product, is enhanced at said conductive metal layer relative to the bulk solution of said first chamber.

2. The method of claim 1 said conductive metal is selected from the group consisting of gold, platinum, silver, rhodium, iridium, ruthenium, palladium, osmium and copper.

3. The method of claim 1 within said first capture antibody layer comprises a first antibody which specifically binds to an analyte selected from the group consisting of hCG, prostate-specific antigen, creatine phosphokinase, troponin, myoglobin, light-chain myosin, fibrinogen, thyroid stimulating hormone, FSH, hepatitis antigen, and viral protein.

4. The method of claim 1 wherein said microporous membrane support further comprises an antibody immobilizing layer, between said conductive metal layer and said capture antibody layer.

5. The method of claim 4 wherein said antibody immobilizing layer is an alkanethiol attached to the conductive metal layer through an -S-H group at one end and having, at the other end, an amino group or a group containing a carbon-oxygen bond for immobilizing said antibody layer,
wherein said alkanethiol has a carbon chain length such that said analytical signal can be enhanced by 2–3 orders of magnitude as compared with said background signal.

6. The method of claim 4 wherein said antibody immobilizing layer is an alkanethiol attached to the conductive metal layer through an -S-H group at one end and having at the other end an amino group or a group containing a carbon-oxygen bond for immobilizing said antibody layer wherein said alkanethiol has a carbon chain length of up to ten carbons.

7. The method of claim 1 wherein mechanical mixing is provided by a stirring device on each side of said microporous membrane support.

8. The method of claim 1 wherein said conductive metal layer is between about 10 and 10,000 Angstroms thick and wherein said microporous membrane support, when coated said conductive metal layer and said capture antibody layer, has a pore size of from about 0.01 to about 10 microns.

9. The method of claim 1 wherein said labeling enzyme is alkaline phosphatase.

10. The method of claim 9 wherein said substrate is an aminophenyl phosphate or nitrophenyl phosphate and wherein said electrochemically detectable species is aminophenol.

11. The method of claim 1 wherein said spatially distinct area of the microporous membrane support is surrounded by a layer of insulating material on said microporous membrane support.

12. The method of claim 11 wherein said test sample is whole blood.

13. The method of claim 1 wherein said coating of said microporous membrane support further comprises a second capture antibody layer comprising a second antibody immobilized over said conductive metal layer in a second spatially distinct area of said microporous membrane support wherein said first antibody specifically binds to a first analyte and said second antibody specifically binds to a different second analyte.

14. The method of claim 13 wherein said first and second analytes are independently selected from the group consisting of creatine phosphokinase-MB, troponin, myoglobin, fibrinogen, and light-chain myosin.

* * * * *